United States Patent
El-Fahmawi

(10) Patent No.: US 9,138,205 B2
(45) Date of Patent: Sep. 22, 2015

(54) SAMPLE RECOVERY AND COLLECTION DEVICE

(71) Applicant: Mawi DNA Technologies LLC, Newark, CA (US)

(72) Inventor: Bassam El-Fahmawi, Newark, CA (US)

(73) Assignee: MAWI DNA TECHNOLOGIES LLC, Newark, CA (US)

( * ) Notice: Subject to any disclaimer, the term of this patent is extended or adjusted under 35 U.S.C. 154(b) by 0 days.

(21) Appl. No.: 14/181,873

(22) Filed: Feb. 17, 2014

(65) Prior Publication Data

US 2014/0243706 A1    Aug. 28, 2014

Related U.S. Application Data

(60) Provisional application No. 61/901,914, filed on Nov. 8, 2013, provisional application No. 61/768,362, filed on Feb. 22, 2013.

(51) Int. Cl.
*A61B 10/00* (2006.01)
*A61B 10/02* (2006.01)
*A61F 13/38* (2006.01)

(52) U.S. Cl.
CPC ............. *A61B 10/0096* (2013.01); *A61B 10/02* (2013.01); *A61F 13/38* (2013.01)

(58) Field of Classification Search
CPC ....... C12M 1/30; C12M 33/02; B01L 3/5029; A61B 10/0096
USPC ................. 73/864.91; 600/572, 569
See application file for complete search history.

(56) References Cited

U.S. PATENT DOCUMENTS

| 4,390,298 | A  | * | 6/1983 | Carluccio ...................... 401/122 |
| 6,291,234 | B1 | * | 9/2001 | Raz et al. .................... 435/309.1 |
| 6,890,484 | B2 |   | 5/2005 | Bautista et al. |
| 7,691,326 | B2 |   | 4/2010 | Sorenson et al. |
| 2003/0129738 | A1 | * | 7/2003 | Sorenson et al. .......... 435/287.1 |
| 2004/0175224 | A1 | * | 9/2004 | Hermansen et al. .......... 401/126 |
| 2010/0129133 | A1 | * | 5/2010 | De Laforcade .............. 401/122 |
| 2010/0203547 | A1 | * | 8/2010 | Anderson et al. ................. 435/6 |
| 2011/0212002 | A1 | * | 9/2011 | Curry et al. .................... 422/430 |

FOREIGN PATENT DOCUMENTS

| WO | 97/19335 | 5/1997 |
| WO | 99/53850 | 10/1999 |
| WO | 2010020043 | 2/2010 |

OTHER PUBLICATIONS

International Search Report and Written Opinion for International Application No. PCT/US14/16699 dated May 12, 2014 (25 pages).

* cited by examiner

*Primary Examiner* — Brian Szmal
(74) *Attorney, Agent, or Firm* — Michael Best & Friedrich LLP

(57) ABSTRACT

Disclosed herein is a sample recovery and collection device comprising a tube, a cap, an insert, and an opening. The cap includes an O-ring and is removably secured to the tube for sealing the tube. The insert includes a first end having a ring that is adhered to the tube and second end opposite the first end. The insert also includes a first leg, a second leg, and a third leg, each coupled to and extending from the ring to the second end. The opening extends from the ring to the second end and the insert defines a diameter. Also disclosed herein is a kit comprising the sample recovery and collection device. Further disclosed herein is a method of collecting a sample from a subject.

4 Claims, 13 Drawing Sheets

■ Bacteria DNA
▨ Buccal Cell DNA

SAMPLE RECOVERY AND COLLECTION DEVICE

CROSS-REFERENCE TO RELATED APPLICATIONS

This claims priority to U.S. Patent Application No. 61/768,362, filed on Feb. 22, 2013, and U.S. Patent Application No. 61/901,914, filed on Nov. 8, 2013, the entire contents of all of which are fully incorporated herein by reference.

TECHNICAL FIELD

The present invention relates to a sample recovery and collection device. In particular, the device includes a mechanism for more efficiently extracting and adding a collected sample to a solution for transportation and storage.

BACKGROUND

Biological specimens or samples are routinely required by predicting or diagnosing a disease or condition in a subject in need thereof. The samples may be collected in a medical facility (e.g., hospital or clinic) or in any number of environments, for example, in the subject's home, work and community. Samples, such as buccal, nasopharyngeal, wounds, blood spatter or drops, etc., can be collected with absorbent material (e.g., swab) and the use of swabs allows for non-invasive sample collection.

The current devices and methods for obtaining, storing, and transporting a sample typically allow only a single swab (or at most, two swabs) to be used per subject. The swab may be transported in a specialized transport medium or in a mail envelope, but such transport may compromise the integrity of the sample. Each swab has a limited surface area for sample collection, and thus, providing one or two swabs (at most) often results in insufficient material for diagnostic testing. Additionally, inefficient isolation of the sample from the swab results in low sample output for diagnostic testing. Many times, the subject is required to re-submit one or more additional samples, thereby reducing compliance by the subject.

Accordingly, a need exists for improved devices and methods for sample collection to facilitate prediction and/or diagnosis of a disease or condition in the subject in need thereof.

SUMMARY

The present invention is directed to a sample recovery and collection device comprising a tube, a cap, an insert, and an opening. The cap may include an O-ring and may be removably secured to the tube for sealing the tube. The insert may include a first end having a ring that is adhered to the tube and a second end opposite the first end. The insert may also include a first leg, a second leg, and a third leg, each coupled to and extending from the ring to the second end. The opening may extend from the ring to the second end and the insert may define a diameter.

The sample recovery and collection device may further comprise a solution enclosed within the tube. The opening of the insert may be configured to receive a swab and apply pressure to a tip of the swab. The pressure exerted on the tip of the swab may cause a sample carried by the swab tip to be squeezed into the tube to mix with a solution enclosed within the tube.

The diameter may be widest near the first end of the insert and the diameter may be narrowest at the second end. Each of the first, second and third legs may include a plurality of protrusions that project radially from an inside surface of each of the legs. The sample recovery and collection device may further comprise a box holder and box. The box holder may be configured to receive and secure the device within the box.

The present invention is also directed to a sample recovery and collection device comprising a tube, a solution, and a cap. The tube may include a tapered opening. The solution may be enclosed in the tube. The cap may include an O-ring and may be removably secured to the tube for sealing the tube.

The tapered opening may be configured to receive a swab and apply pressure to a tip of the swab. The pressure exerted on the tip of the swab may cause a sample carried by the swab tip to be squeezed into the tube to mix with the solution. The tapered opening may be defined by a first leg, a second leg, and a third leg. Each of the legs may be spaced apart from an inner wall of the tube. Each of the legs may be substantially conically shaped and include a plurality of protrusions on an inner surface.

The present invention is further directed to a kit comprising a sample recovery and collection device. The sample recovery and collection device may comprise a tube, a cap, an insert, and an opening. The cap may include an O-ring and may be removably secured to the tube for sealing the tube. The insert may include a first end having a ring that is adhered to the tube and a second end opposite the first end. The insert may also include a first leg, a second leg, and a third leg, each coupled to and extending from the ring to the second end. The opening may extend from the ring to the second end and the insert may define a diameter. The kit may further comprise one or more swabs.

The present invention is directed to a method of collecting a sample from a subject. The method comprises providing a sample recovery and collection device. The sample recovery and collection device may comprise a tube, a cap, an insert, and an opening. The cap may include an O-ring and may be removably secured to the tube for sealing the tube. The insert may include a first end having a ring that is adhered to the tube and a second end opposite the first end. The insert may also include a first leg, a second leg, and a third leg, each coupled to and extending from the ring to the second end. The opening may extend from the ring to the second end and the insert may define a diameter.

The method may also comprise contacting a tip of a swab against a body portion of the subject to obtain the sample, inserting the swab tip through the opening of the insert, and transferring the sample from the swab tip to a solution enclosed within the tube. The sample may comprise buccal cells. Inserting may further comprise applying pressure to the swab tip to cause the sample to be squeezed from the swab tip into the tube to mix with the solution.

The method may further comprise contacting a tip of a second swab against the body portion of the subject to obtain a second sample, inserting the second swab tip through the opening of the insert, and transferring the second sample from the second swab tip to the solution enclosed within the tube.

DETAILED DESCRIPTION

Figure 1:
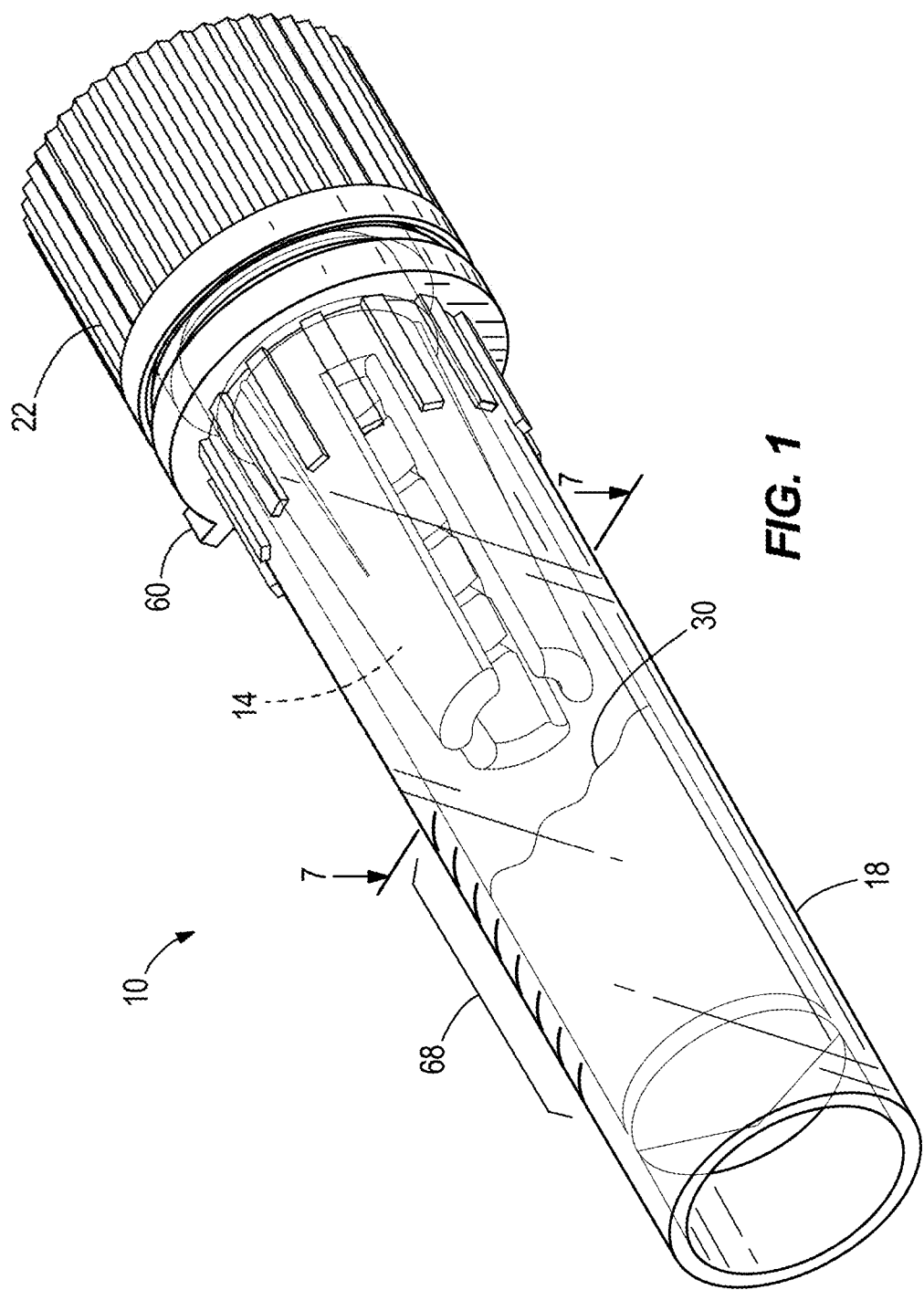
FIG. 1 is a perspective view of a sample recovery and collection device including a tube, an insert, and a cap according to one embodiment of the invention.

The present invention relates to a sample recovery and collection device that more efficiently collects a sample, for example, buccal cells from a swab tip. The sample recovery and collection device includes an insert that applies a squeezing force on the swab tip to cause removal of the buccal cells from the swab tip. The pressure from the squeezing force may be about 0.1 pounds per square inch (PSI) to about 10 PSI or about 0.007 kg/cm$^2$ to about 0.70 kg/cm$^2$. Via this squeezing force, the insert causes about 100% transfer of the buccal cells from the swab tip to a solution within the sample recovery and collection device.

Accordingly, the sample recovery and collection device efficiently collects the sample by minimizing sample loss when the buccal cells are transferred from the swab tip to the sample recovery and collection device. In turn, more buccal cells are available for downstream applications that are used to monitor and diagnose disease. Such downstream applications may include DNA extraction, RNA extraction, protein extraction, and/or amplification. By more efficiently collecting the sample, DNA yield, RNA yield, and/or protein yield from a single collection with the sample recovery and collection device may be increased over DNA yield, RNA yield, and/or protein yield from a sample obtained by normal collection with a swab and placement in a suspension medium. For example, DNA yield from a sample obtained with the sample recovery and collection device may be increased by about 5.8-fold over the DNA yield from the sample obtained by normal collection. Accordingly, the sample recovery and collection device facilitates the collection of significantly more sample in a single collection for use in one or more diagnostic tests.

The sample recovery and collection device also minimizes bacterial contamination of the sample, even when the sample is collected in a non-sterile environment. The sample recovery and collection device may minimize bacterial contamination to less than about 1% of the total collected sample. Accordingly, the sample recovery and collection device efficiently collects the sample while minimizing bacterial contamination of the sample.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "subject" or "patient" as used herein interchangeably means any vertebrate, including, but not limited to, a mammal (e.g., cow, pig, camel, llama, horse, goat, rabbit, sheep, hamsters, guinea pig, cat, dog, rat, mouse, and a non-human primate (for example, a monkey, such as a cynomolgous or rhesus monkey, chimpanzee, etc.)) and a human. In some embodiments, the subject or patient may be a human or non-human. The subject or patient may or may not be undergoing treatment for a disease. In some embodiments, the subject or patient may be a human subject at risk for developing or already having a disease.

The term "sample," "test sample," "specimen," "biological sample," "biological specimen," "sample from a subject," or "subject sample" as used herein interchangeably, means a sample or isolate of tissue or cell(s) can be used directly as obtained from a subject or can be pre-treated, such as by filtration, distillation, extraction, concentration, centrifugation, inactivation of interfering components, addition of reagents, and the like, to modify the character of the sample in some manner as described herein or otherwise known in the art. The sample may be any tissue or cell sample taken or derived from the subject. In some embodiments, the sample from the subject may comprise protein, nucleic acid (e.g., RNA and/or DNA), lipid, and/or polysaccharide. Any cell type, tissue, or bodily fluid may be utilized to obtain a sample. The tissue may be, for example, but not limited to, cheek tissue, tongue tissue, nasal tissue, skin tissue, throat tissue, rectal tissue, vaginal tissue, cervical tissue, or any other tissue obtainable by contact with a swab or the like. The bodily fluid may be, for example, but not limited to, blood drops or spatter, saliva, urine, mucus, or any other bodily fluid obtainable by contact with a swab or the like.

The term also means any biological material being tested for and/or suspected of containing an analyte of interest, for example, but not limited to, DNA, RNA, protein(s), lipid(s), antibodies, antigens, modified proteins (e.g., glycosylated, phosphorylated, ubiquitinated, sumolyated, and other modifications known in the art), or other cellular components that can be used to measure and provide diagnostic avenues for predicting or diagnosing any disease or condition of a subject in need thereof. The sample can comprise further moieties in addition to the analyte of interest such as antibodies, antigens, haptens, hormones, drugs, enzymes, receptors, proteins, peptides, polypeptides, oligonucleotides, or polynucleotides.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Sample Recovery and Collection Device

Described herein is a sample recovery and collection device 10 that may obtain a plurality of samples from a single patient and concentrate the samples for suspension in a proper transport medium (hereinafter also known as a "sample suspension solution," "suspension solution," or "suspension medium") for further diagnostic tests. The sample recovery and collection device 10 may be known as the collection device 10. The collection device 10 provides an 80%, 81%, 82%, 83%, 84%, 85%, 86%, 87%, 88%, 89%, 90%, 91%, 92%, 93%, 94%, 95%, 96%, 97%, 98%, 99% or about a 100% transfer of the sample from a swab 146 to the collection device 10 to the sample suspension solution 30. The transfer of the sample from the swab 146 to the collection device 10 to the sample suspension solution 30 may increase yield of the sample 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold over normal collection by a swab and placing in a solution. As described above, the sample may be any biological material including, but not limited to, DNA, RNA, proteins, fatty acids, lipids, and other cellular components that can be used to measure and provide diagnostic avenues for predicting or diagnosing any disease or condition of a subject in need thereof.

Figure 3:
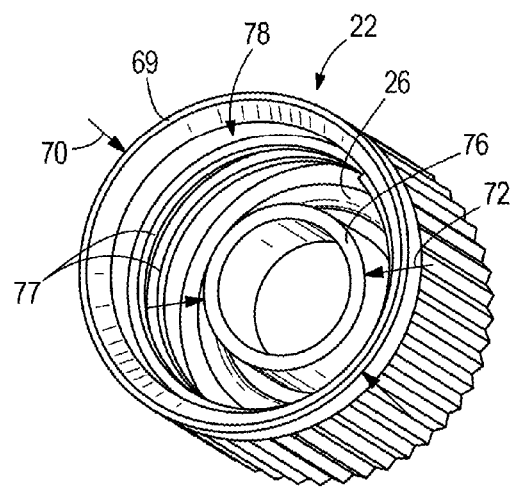
FIG. 3 is a bottom perspective view of the cap of FIG. 1.
Figure 4:
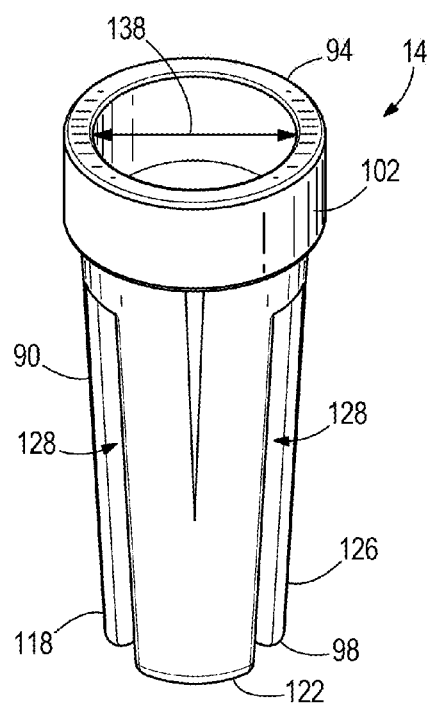
FIG. 4 is a perspective view of the insert of FIG. 1.
Figure 5:
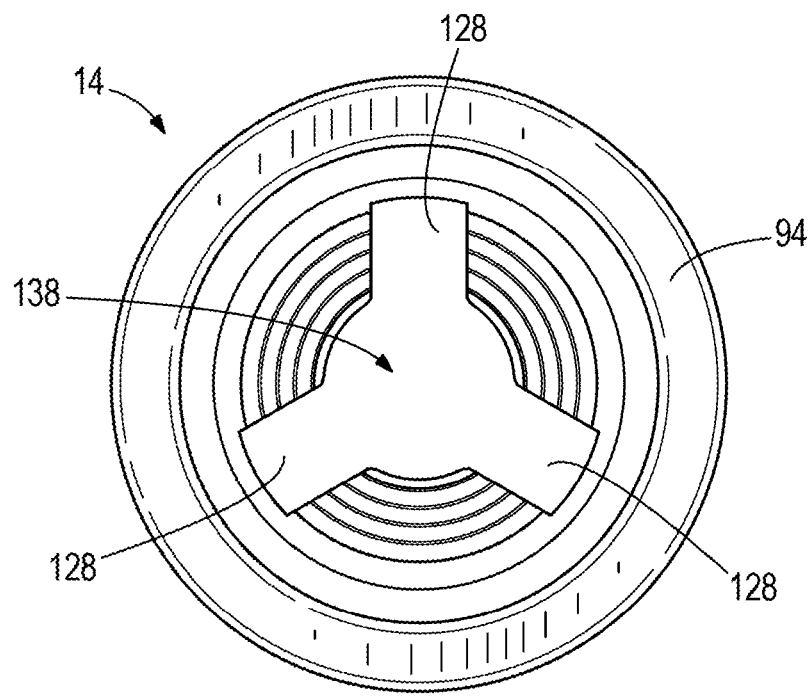
FIG. 5 is a top view of the insert of FIG. 1
Figure 6:
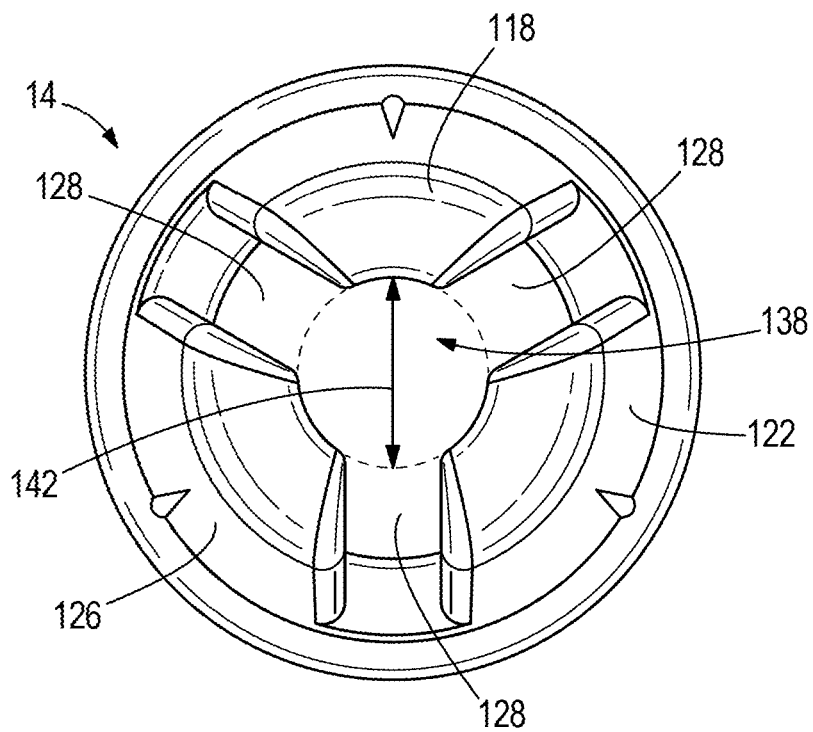
FIG. 6 is a bottom view of the insert of FIG. 1.
Figure 7:
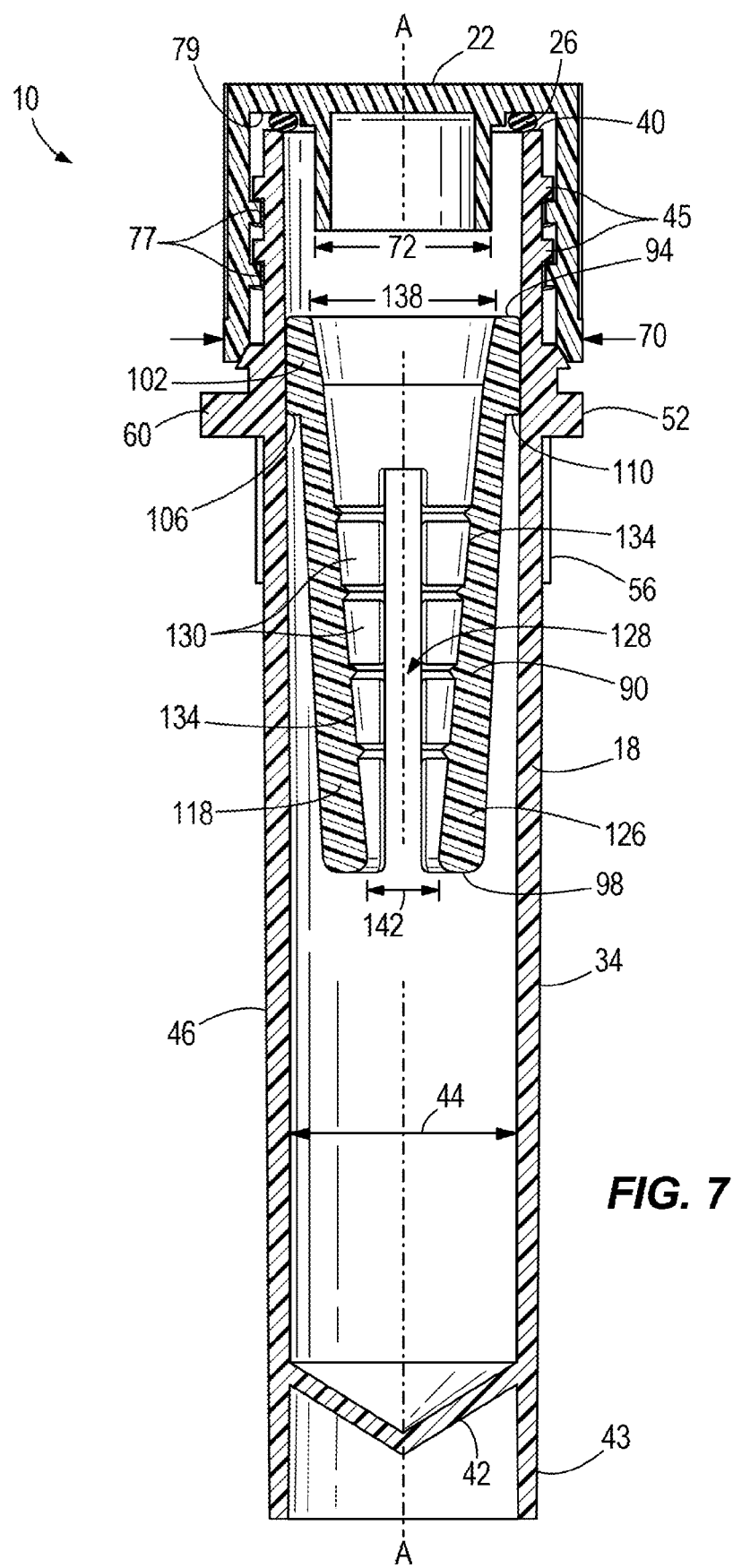
FIG. 7 is a cross-sectional view of the device of FIG. 1 along the sectional line 7-7.

The collection device 10 defines a longitudinal axis A and includes an extraction and squeezing insert 14, a self-standing graduated tube 18, and a cap 22 with an O-ring 26 (FIGS. 3 and 7). When assembled, the extraction and squeezing insert 14 is positioned inside the self-standing graduated tube 18 along with a sample suspension solution 30. The cap 22 threadingly secured to the tube 18 to seal the tube 18.

Figure 2:
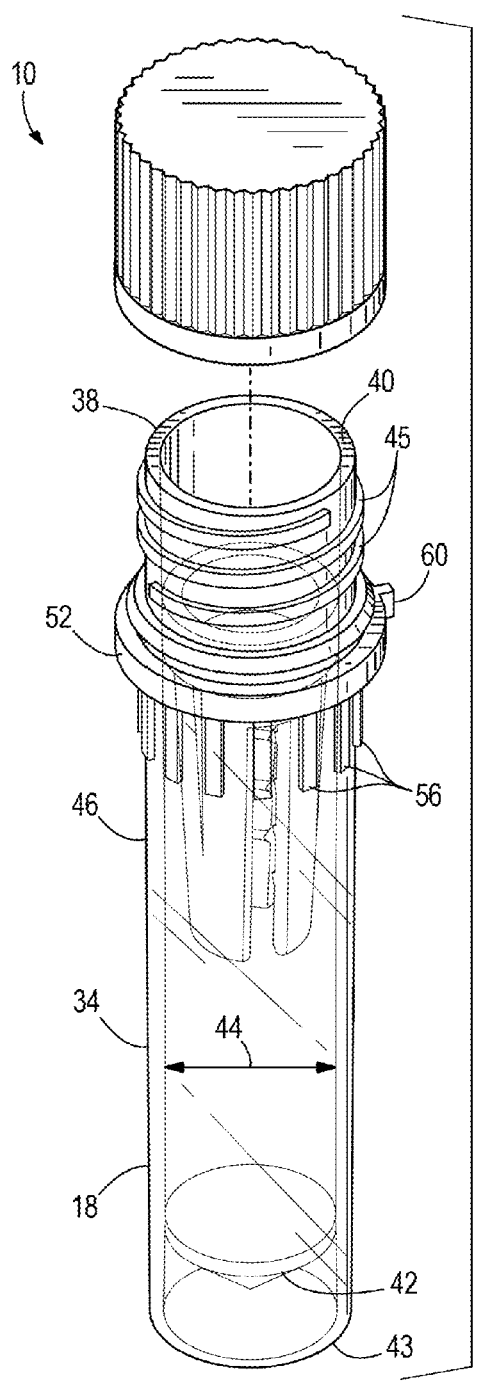
FIG. 2 is an exploded view of the device of FIG. 1.

FIGS. 1, 2, and 7 illustrate the tube 18, which in the illustrated embodiment is self-standing graduated tube 18 (hereafter referred to as the "tube" or "device tube"), which matches with cap 22. The tube 18 includes a body 34 having an open first end 38 and a closed second end 42, which is opposite the first end 38. In the illustrated embodiment, a portion 43 the body 34 extends beyond the second end 42. In other embodiments the body 34 may not extend beyond the second end 42. The body defines a first diameter 44. The open end 38 includes a rim 40 and threads 45 on an exterior surface 46. The exterior surface 46 of the tube 18 also includes a circumferential lip 52 having integrally formed projections 56 descending therefrom. At least one protuberance 60 extends radially from the lip 52. The projections 56 are circumferentially spaced about the body 34 of the tube 18. As shown, the tube 18 is used for the containment of the sample for transportation and storage purposes. The second end 42 of each tube 18 has a unique identifier (not shown) for tracking and sample retrieval process. The unique identifier can be a bar code, a QR code, or any of several encoded symbols which when scanned can identify the tube 18. The tube 18 also includes a graduated scale 68 on the body 34 of the tube 18.

With respect to FIGS. 1-3, and 7, the cap 22 includes the O-ring 26 and is removably positioned over the tube 18 to provide a tight seal for protection during transportation or storage. The cap 22 includes a cylindrical wall 69, which is defined by a first diameter 70 that is sized to surround the tube 18. The cap 22 also includes a hollow, cylindrical projection 76 that defines a second diameter 72. A recess 78 is formed between the wall 69 and the projection 76. The O-ring 26 is seated within the recess 78. The tight seal is formed by the threaded coupling between threads 77 on the cap 22 and the threads 45 on the tube 18 as well as the O-ring 26 on the cap 22. When the cap 22 is assembled with the tube 18, the recess 78 receives the rim 40 of the tube 18 such that the O-ring 26 is pressed between the rim 40 of the tube 18 and an upper, interior surface 79 of the cap 22. The cap 22 minimizes the chance that sample loss by leakage or evaporation will occur. Sample loss can be visually measured by using the graduation scale 68 on the tube 18. In additional or alternative embodiments, the mating interface between the tube 18 and the cap 22 may have different configurations (i.e., press-fit engagement, snap-fit engagement, corked engagement, etc.).

With reference to FIGS. 1, 2, and 4-7, the extraction and squeezing insert 14 (hereafter referred to as the "insert" or "device insert"). As shown, the insert 14 includes a body 90 including a first end 94 and a second end 98. The first end 94 of the body 90 includes a ring 102 with two protrusions 106, 110 on at least two sides of the ring 102. The ring 102 is secured with the tube 18 and therefore, a tight seal between the insert 14 and the tube 18 is established. The seal between the insert 14 and the tube 18 ensures that the insert 14 remains in place during the process of pushing in and taking out a swab 146, which will be described in greater detail below. It should be understood that, in some embodiments, the insert 14 may be altered to fit (or be positioned) within any number of tubes 18 that may vary from one another in size (e.g., the first diameter 44 may increase or decrease in the tube 18), thereby maintaining the tight seal between the insert 14 and any tube 18 that has changed in size. The first end 94 defines a first diameter 138 that may be sized and shaped to receive the projection 76 of the cap 22. The body 90 also includes first, second, and third legs 118, 122, 126, which constitute a squeezing mechanism, which will be described in greater detail below. The legs 118, 122, 126 are spaced apart by openings 128. Additionally, the legs 118, 122, 126 extend from the ring 102 to the second end 98 of the body 90. Each of the legs 118, 122, 126 includes a plurality of protrusions 130 on an interior surface 134. An opening or channel 138 extends through the insert 14 from the first end 94 to the second end 98. The opening 138 is tapered. The first diameter 114 is also the widest diameter of the opening 138. The diameter of the insert tapers to a narrowest diameter 142 at the second end 98 of the insert 14. The opening 138 receives a swab 146, having a swab tip 146a (FIGS. 8 and 10), as described in more detail below. The swab tip 146a can be any material commonly used for swabs, including cotton, rayon, standard polyester, flocked polyester, etc.

The insert 14 imparts a firm and uniform squeeze on the swab 146 consistently along the opening 138. The insert 14, therefore, causes substantial pressure on the swab 146 to maximize the amount of sample recovered from the swab 146, both before and after suspension in the sample suspension solution 30. The legs 118, 122, 126 of the insert 14 allow for the squeezing process to occur when the swab 146 is going into and being removed from the solution 30 in the tube 18. The plurality of protrusions 130 on each leg 118, 122, 126 are designed to exert extra sectional squeezing on the swab 146 on its way in and out of the tube 18. In other words, the tapered opening 138, together with protrusions 130, imparts a force (and therefore a pressure) on the swab 146 that increases as swab 146 moves from the first end 38 of the tube 18 towards the sample suspension solution 30 at the second end 42 of the tube 18. Therefore, the pressure on the swab 146 will be the smallest near the top 38 of the tube, while the pressure on the swab 146 at the second end 98 of the insert 14 will be the greatest. Accordingly, the pressure will increase from the smallest pressure to the greatest pressure. The pressure along the opening 138 of the insert 14 may be in a range of approximately 0.1 pounds per square inch (PSI) to approximately 10 PSI. For example, the pressure at any point along the opening 138 of the insert 14 may be about 0.1 PSI, 0.2 PSI, 0.3 PSI, 0.4 PSI, 0.5 PSI, 0.6 PSI, 0.7 PSI, 0.8 PSI, 0.9 PSI, 1.0 PSI, 1.1 PSI, 1.2 PSI, 1.3 PSI, 1.4 PSI, 1.5 PSI, 1.6 PSI, 1.7 PSI, 1.8 PSI, 1.9 PSI, 120 PSI, 2.1 PSI, 2.2 PSI, 2.3 PSI, 2.4 PSI, 2.5 PSI, 2.6 PSI, 2.7 PSI, 2.8 PSI, 2.9 PSI, 3.0 PSI, 3.1 PSI, 3.2 PSI, 3.3 PSI, 3.4 PSI, 3.5 PSI, 3.6 PSI, 3.7 PSI, 3.8 PSI, 3.9 PSI, 4.0 PSI, 4.1 PSI, 4.2 PSI, 4.3 PSI, 4.4 PSI, 4.5 PSI, 4.6 PSI, 4.7 PSI, 4.8 PSI, 4.9 PSI, 5.0 PSI, 6.1 PSI, 6.2 PSI, 6.3 PSI, 6.4 PSI, 6.5 PSI, 6.6 PSI, 6.7 PSI, 6.8 PSI, 6.9 PSI, 7.0 PSI, 7.1 PSI, 7.2 PSI, 7.3 PSI, 7.4 PSI, 7.5 PSI, 7.6 PSI, 7.7 PSI, 7.8 PSI, 7.9 PSI, 8.0 PSI, 8.1 PSI, 8.2 PSI, 8.3 PSI, 8.4 PSI, 8.5 PSI, 8.6 PSI, 8.7 PSI, 8.8 PSI, 8.9 PSI, 9.0 PSI, 9.1 PSI, 9.2 PSI, 9.3 PSI, 9.4 PSI, 9.5 PSI, 9.6 PSI, 9.7 PSI, 9.8 PSI, 9.9 PSI, or 10.0 PSI. The pressure at any point along the opening 138 of the insert 14 may be about 0.007 kg/cm$^2$ to about 0.70 kg/cm$^2$. The pressure at any point along the opening 138 of the insert 14 may be about 0.008 kg/cm$^2$, about 0.009 kg/cm$^2$, about 0.01 kg/cm$^2$, about 0.02 kg/cm$^2$, about 0.03 kg/cm$^2$, about 0.04 kg/cm$^2$, about 0.05 kg/cm$^2$, about 0.06 kg/cm$^2$, about 0.07 kg/cm$^2$, about 0.08 kg/cm$^2$, about 0.09 kg/cm$^2$, about 0.1 kg/cm$^2$, about 0.2 kg/cm$^2$, about 0.3 kg/cm$^2$, about 0.4 kg/cm$^2$, about 0.5 kg/cm$^2$, about 0.6 kg/cm$^2$, or about 0.7 kg/cm$^2$.

As discussed above, the opening 138 of the insert 14 is tapered and related to the sizes of the tips of the majority of common swabs 146 used in the field, as well as the accessibility of a standard pipette tip for maximum sample retrieval. In the illustrated embodiment, first, second, and third legs 118, 122, 126 that are substantially conically shaped and include approximately 3 projections. In additional or alternative embodiments, the legs may be shaped differently and there may be greater or fewer legs and/or greater or fewer protrusions than illustrated herein.

FIGS. 1 and 7 illustrate a fully assembled collection device 10. The assembled collection device 10, as shown, includes the insert 14 inside the tube 18 with the sample suspension solution 30 and the tube 18 tightly seal with the matching cap 22.

3. Method of Collection

Figure 10:
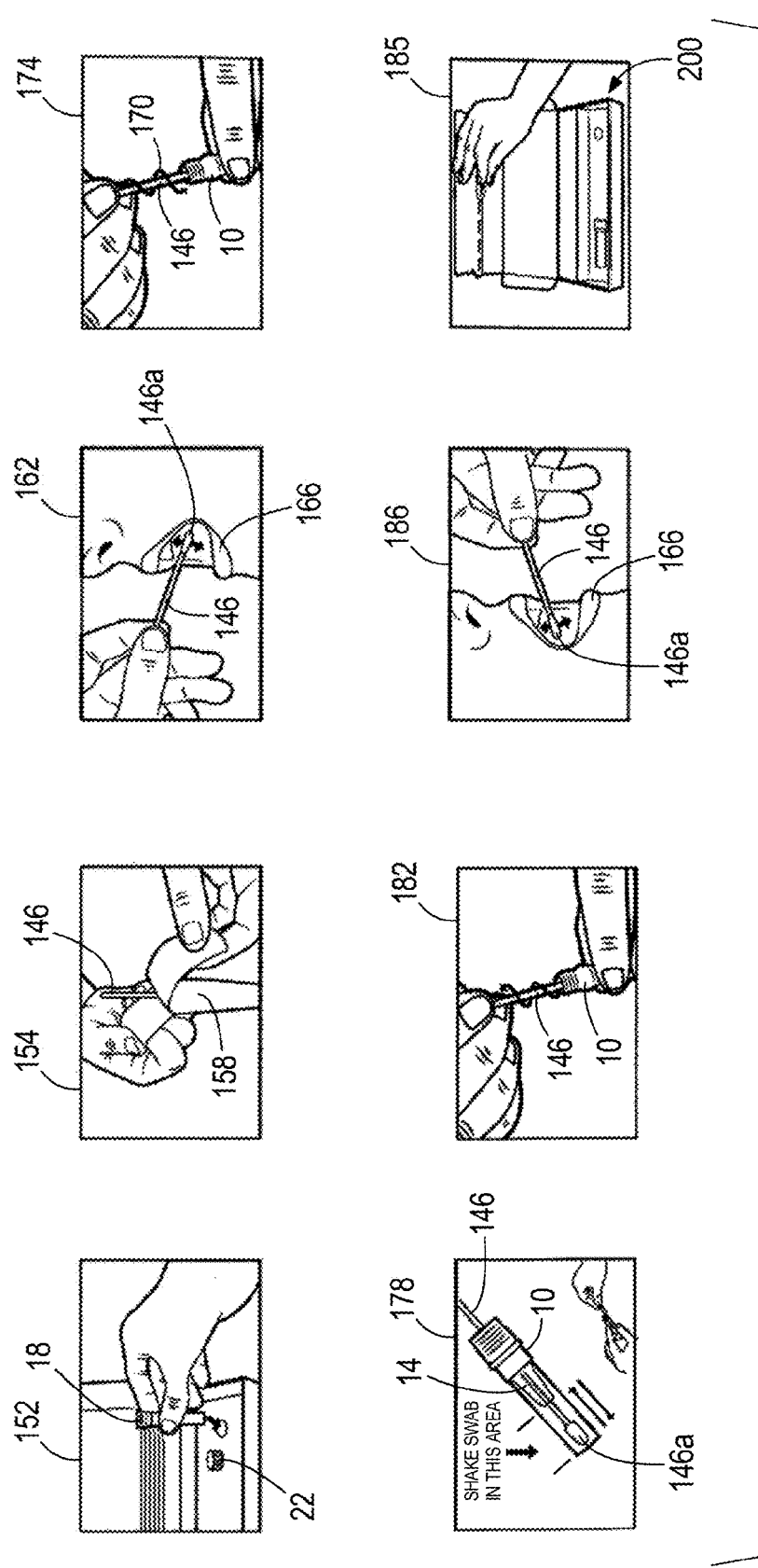
FIG. 10 illustrates an exemplary process of obtaining a sample using the device of FIG. 1.

The collection device 10 may be used in a method for collecting, obtaining, and isolating a plurality of samples from a single patient. FIG. 10 conceptually illustrates a process 150 for obtaining and concentrating the sample using the collection device 10 of some embodiments. As shown, the process includes a plurality of steps. First, the process 150 includes a step opening (i.e., unscrewing) the cap 22 from the tube 18 to provide the access to the sample suspension solution 30 (at 152) therein and for peeling (at 154) off a swab pouch 158, which contains the swab 146. The swab pouch 158 can be peeled off to reveal the swab tip 146a. After the swab pouch 158 is peeled, the next step of the process 150 is to apply (at 162) the swab tip 146a to a body portion of the a subject (e.g., the inside of a subject's cheek 166) and rub the swab tip 146a against the cheek 166 for a period of time. In some embodiments, the subject to which the swab 146 is applied is a patient as described above. The period of time in different embodiments can vary, but in all embodiments, a minimum time of ten seconds is required to obtain a sufficient sample from the subject. The period of time, in which the swab tip 146a is rubbed against the cheek 166, may be at least about 10 seconds, about 11 seconds, about 12 seconds, about 13 seconds, about 14 seconds, about 15 seconds, about 16 seconds, about 17 seconds, about 18 seconds, about 19 seconds, about 20 seconds, about 21 seconds, about 22 seconds, about 23 seconds, about 24 seconds, about 25 seconds, about 26 seconds, about 27 seconds, about 28 seconds, about 29 seconds, about 30 seconds, about 31 seconds, about 32 seconds, about 33 seconds, about 34 seconds, about 35 seconds, about 36 seconds, about 37 seconds, about 38 seconds, about 39 seconds, about 40 seconds, about 41 seconds, about 42 seconds, about 43 seconds, about 44 seconds, about 45 seconds, about 46 seconds, about 47 seconds, about 48 seconds, about 49 seconds, about 50 seconds, about 51 seconds, about 52 seconds, about 53 seconds, about 54 seconds, about 55 seconds, about 56 seconds, about 57 seconds, about 58 seconds, about 59 seconds, or about 60 seconds. The period of time, in which the swab tip 146a is rubbed against the cheek 166, may be at least about 30 seconds.

Once the sample is obtained on the swab tip 146a, the process 150 further includes a step for inserting (at 174) the swab 146 into the tube 18 with light force and/or a twisting motion as indicated by reference 170, for example. The design of the collection device 10 necessarily causes some resistance to the swab tip 146a as the swab 146 is inserted into the tube 18 through the opening 104 in the insert 14. The resistance results in a squeezing force being applied to the pre-wetted sample with buccal cells before entering the sample suspension solution 30 at the second end 42 of the tube 18.

The squeezing force applied by the insert 14 efficiently removes the sample from the swab tip 146a into the sample suspension solution 30. The insert 14 may cause about 80% to about 100%, about 85% to about 100%, about 90% to about 100%, or about 95% to about 100% transfer of the sample from the swab tip 146a to the sample suspension solution 30. The insert 14 may cause about 90%, about 91%, about 92%, about 93%, about 94%, about 95%, about 96%, about 97%, about 98%, about 99%, or about 100% transfer of the sample from the swab tip 146a to the sample suspension solution 30.

The process 150 also includes a step for shaking (at 178) the tip 146a of the swab 146 in the sample suspension solution 30 for a minimum period of time (i.e., minimum of twenty seconds) by moving the tip 146a up and down but not removing the swab 146 from the insert 14. Upon completion of steps of the process 150, the sample is fully concentrated in the sample suspension solution 30. Thus, the process includes a step (at 182) at this point for removing the swab 146 from the tube 30 by pulling and/or twisting the swab 146 upwards until the swab 146 is fully removed from the tube 18. The process 150 next includes discarding (at 186) the used swab 146. The tube 18 is then resealed by the cap 22 such that the tube 18 can be transported or stored appropriately. After steps of the process 150 are completed for a single sample on a single swab 146, the process 150 can end and the collection device 10 is appropriately transported and/or stored 185. The process 150 provides about 90%, about 91%, about 92%, about 93%, about 94%, about 95%, about 96%, about 97%, about 98%, about 99%, or about 100% compliance by the subject from which the sample is obtained.

Alternatively, additional samples collected from additional swabs 146 can be mixed with sample suspension solutions 30 in additional collection devices 10. In still other embodiments, multiple swabs 146 may be employed to collect further samples for concentration 186. For each additional sample that needs to be collected, a new swab 146 is used to perform steps of the process 150. The process 150 can be repeated until a concentrated sample is obtained from a patient. Accordingly, the respective samples from one or more swabs 146 may be transferred to the collection device 10 to the sample suspension solution 30 therein, thereby concentrating the respective samples from the one or more swabs 146 in the sample suspension solution 30. The respective samples from 1 swab 146, 2 swabs 146, 3 swabs 146, 4 swabs 146, 5 swabs 146, 6 swabs 146, 7 swabs 146, 8 swabs 146, 9 swabs 146, or 10 swabs 146 may be transferred to the collection device 10 to the sample suspension solution 30 therein, thereby concentrating the collected sample in the sample suspension solution 30. The respective samples from 4 swabs 146 may be transferred to the collection device 10 to the sample suspension solution 30 therein, thereby concentrating the respective samples from the 4 swabs 146 in the sample suspension solution 30.

As discussed above, the insert 14 facilitates more efficient transfer of the sample from the swab tip 146a to the sample suspension solution 30. Because the sample is efficiently transferred to the sample suspension solution 30, a larger or increased amount of sample is available for downstream applications, for example, DNA extraction, RNA extraction, and protein extraction, as compared to an amount of sample provided by normal collection with a swab and placement in a suspension medium. In turn, the increased amount of sample may afford an increased DNA yield, RNA yield, and/or protein yield as compared to the DNA yield, RNA yield, and/or protein yield obtained from the sample provided by normal collection with a swab and placement in a suspension medium.

The DNA yield from the sample obtained with the collection device 10 may be increased over or greater than the DNA yield from the sample obtained by normal collection with a swab and placement in a suspension medium. The DNA yield from the sample obtained with the collection device 10 may be increased by about 2-fold to about 15-fold, about 2-fold to about 14-fold, about 2-fold to about 13-fold, about 2-fold to about 12-fold, about 2-fold to about 11-fold, about 2-fold to about 10-fold, about 2-fold to about 9-fold, about 2-fold to about 8-fold, about 2-fold to about 7-fold, about 2-fold to about 6-fold, about 3-fold to about 15-fold, about 4-fold to about 15-fold, about 5-fold to about 15-fold, about 2.5-fold to about 12-fold, about 3-fold to about 10-fold, about 3.5-fold to about 8-fold, or about 4-fold to about 6-fold over the DNA yield from the sample obtained by normal collection with a swab and placement in a suspension medium. The DNA yield from the sample obtained with the collection device 10 may also be increased by about 2-fold, about 2.5-fold, about 3-fold, about 3.5-fold, about 4-fold, about 4.5-fold, about 5-fold, about 5.1-fold, about 5.2-fold, about 5.3-fold, about 5.4-fold, about 5.5-fold, about 5.6-fold, about 5.7-fold, about 5.8-fold, about 5.9-fold, about 6-fold, about 6.5-fold, about 7-fold, about 7.5-fold, about 8-fold, about 8.5-fold, about 9-fold, about 9.5-fold, about 10-fold, about 11-fold, about 12-fold, about 13-fold, about 14-fold, or about 15-fold over the DNA yield from the sample obtained by normal collection with a swab and placement in a suspension medium. The DNA yield from the sample obtained with the collection device 10 may further be increased by about 5.8-fold over the DNA yield from the sample obtained by normal collection with a swab and placement in a suspension medium.

Additionally, the RNA yield from the sample obtained with the collection device 10 may be increased over or greater than the RNA yield from the sample obtained by normal collection with a swab and placement in a suspension medium. The RNA yield from the sample obtained with the collection device 10 may be increased by about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, or about 15-fold over the RNA yield from the sample obtained by normal collection with a swab and placement in a suspension medium.

The protein yield from the sample obtained from the collection device 10 may be increased over or greater than the protein yield from the sample obtained by normal collection with a swab and placement in a suspension medium. The protein yield from the sample obtained with the collection device 10 may be increased by about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, or about 15-fold over the protein yield from the sample obtained by normal collection with a swab and placement in a suspension medium.

Furthermore, because the sample may not be collected in a sterile environment, the collection device 10 minimizes or reduced bacterial contamination of the sample. The collection device 10 may minimize bacterial contamination to about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, or about 0.1% to about 1% of the total collected sample. The collection device 10 may minimize bacterial contamination to less than about 10%, less than about 9%, less than about 8%, less than about 7%, less than about 6%, less than about 5%, less than about 4%, less than about 3%, less than about 2%, less than about 1%, less than about 0.5% or less than about 0.1% of the total collected sample. The collection device 10 may minimize bacterial contamination to less than about 1% of the total collected sample.

4. Kit

The collection device 10 may be used in a kit. The kit may further comprise instructions for collecting, obtaining, and/or isolating the sample, and one or more buffers for the storage and/or extraction of DNA, RNA, or protein. These one or more buffers may further be located in additional vials in the kit.

Figure 8:
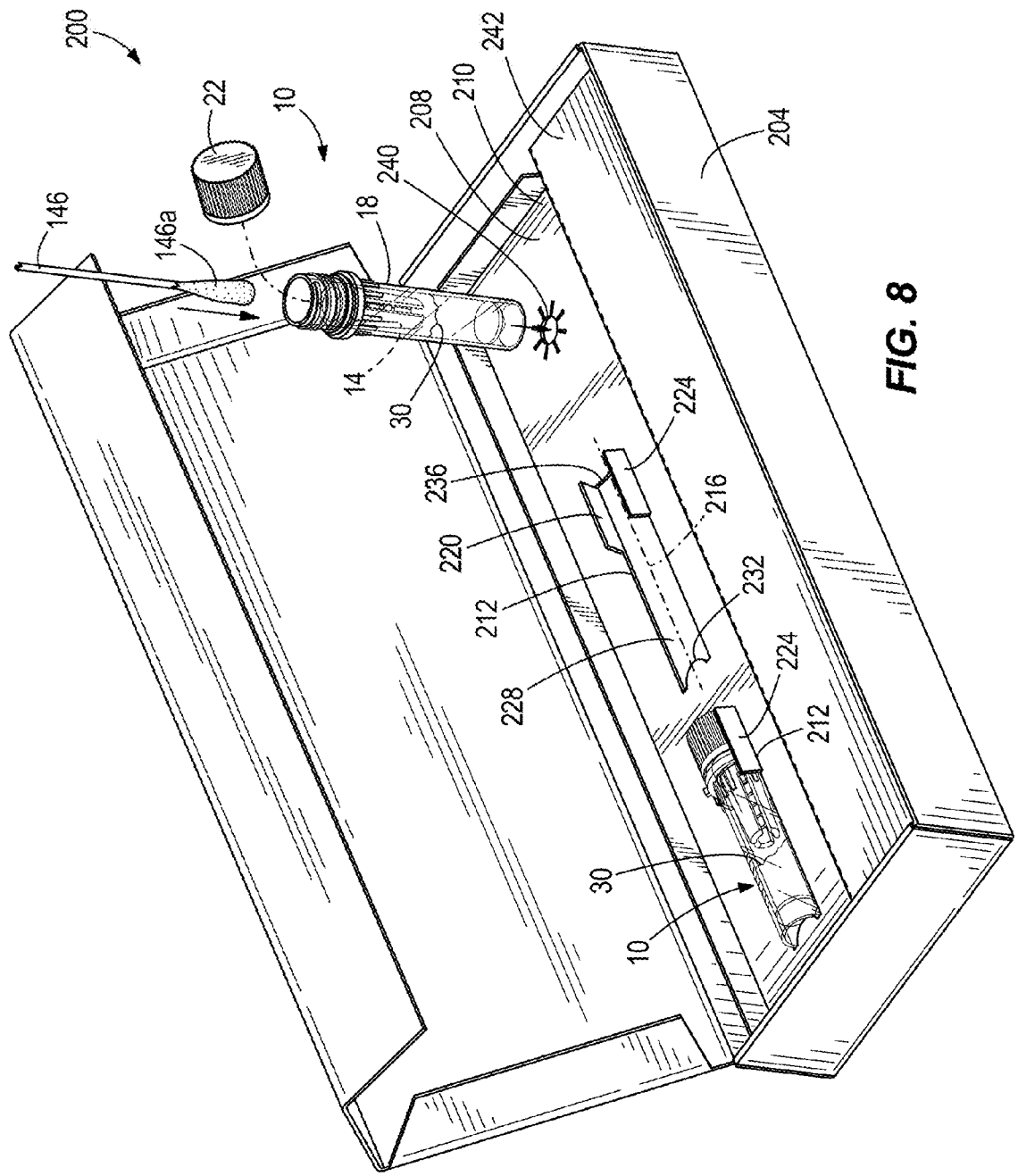
FIG. 8 is a perspective view of a kit including one or more devices of FIG. 1 removably secured to a holder.
Figure 9:
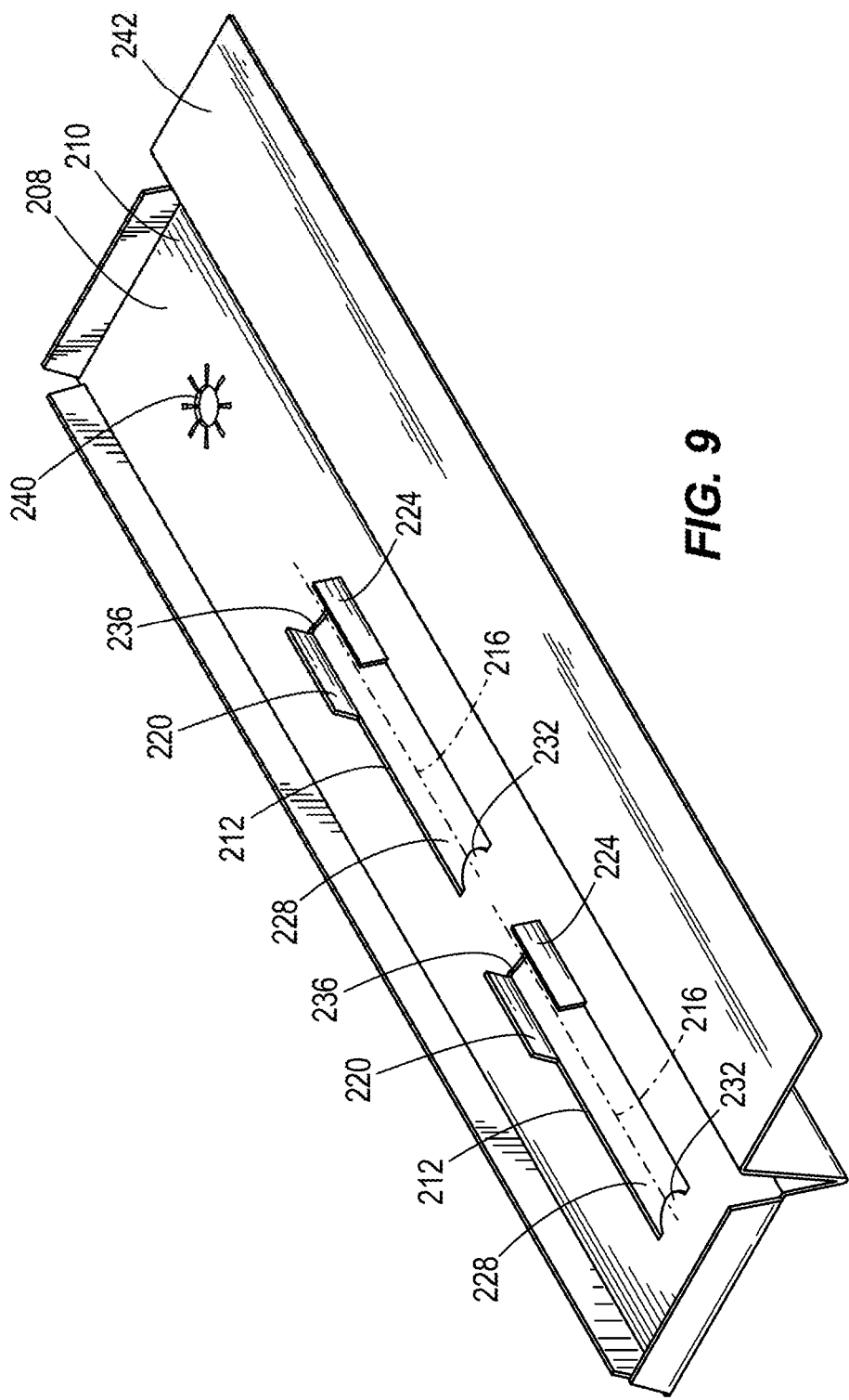
FIG. 9 is a perspective view of the holder of FIG. 8.

FIGS. 8-9 illustrate a kit 200, which includes one or more collection devices 10. The kit 200 includes a box blank 204 that receives a device holder 208. The device holder 208 includes a body 210 that has at least one (although two are illustrated) perforated outlines 212 of the device 10. The perforated outlines 212 may be manipulated to receive the collection device 10. In particular, the perforated outlines 212 are symmetrical about a center line 216. As such, a first side 220 of the perforated outline 212 and a second side 224 of the perforated outline 212 are movable relative to one another. A bottom edge 232 is received by a portion of the second end 42 of the tube, which seats a top of the cap 22 against a top edge 236. The first and second sides 220, 224 and the top and bottom edges 232, 236 create an opening 228 that receives and retains the collection device 10.

The box holder 206 may also include a circular perforated outline 240 that is sized and shaped to hold the tube 18 in a standing orientation, for example during sample collection. The box holder 208 includes a first flap 242 and a second flap 244, which are bendable relative to one another and relative to the body 210 of the holder 208. The flexibility of holder 208 helps to position and retain the holder 208 within the box blank 204 thereby securing the collection device(s) 10 within the box blank 204. As discussed above, the box blank 204 receives the box holder 208, which receives and secures at least one collection device 10, and one or more unused swabs 146 each contained within sealed swab pouch 158. The one or more unused swabs 146 may be 1 swab, 2 swabs, 3 swabs, 4 swabs, 5 swabs, 6 swabs, 7 swabs, 8 swabs, 9 swabs, or 10 swabs. The respective swab tips 146a of the one or more swabs 146 may comprise the same material or different materials. The materials may be, for example, cotton, rayon, standard polyester, and flocked polyester as described above. Accordingly, the kit may include 1 swab 146, 2 swabs 146, 3 swabs 146, 4 swabs 146, 5 swabs 146, 6 swabs 146, 7 swabs 146, 8 swabs 146, 9 swabs 146, or 10 swabs 146 for use in the method of collection described above.

5. Method of Manufacture

Figure 11:
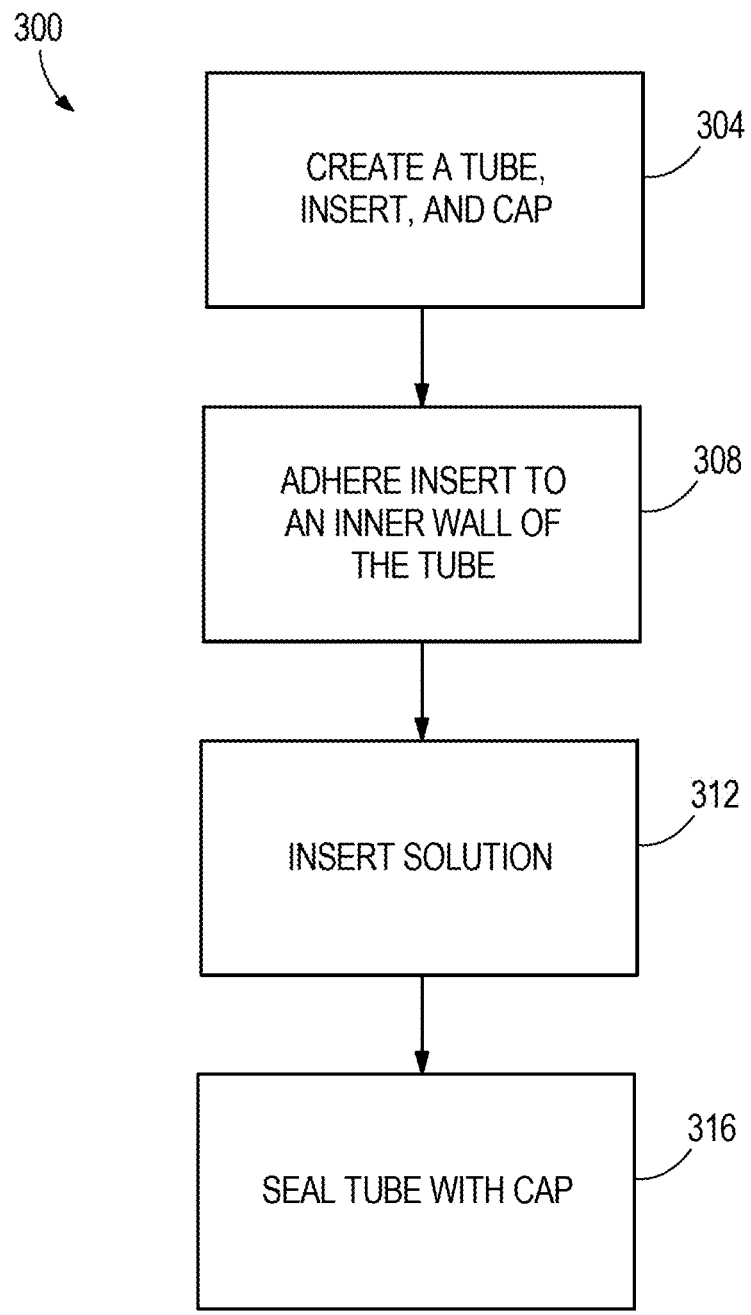
FIG. 11 illustrates a flow chart exemplifying a method of manufacture of the device of FIG. 1.

The collection device 10 may be manufactured in a number of different manners. FIG. 11 illustrates a flowchart of a method 300 for providing or manufacturing the collection device 10. To manufacture the compartment 10, the insert 14, the tube 18 and cap 22 are formed or created at block 304. In the illustrated embodiment, the insert 14, the tube 18, and the cap 22 are all formed from the same plastic; in additional or alternative embodiments, any other material may be used for one or more of the insert 14, the tube 18, and the cap 22 and the material may not be the same for all. At block 308, the insert 14 is inserted into the tube 18 and adhered to an inner wall of the tube 18. The insert 14 may be adhered by any suitable method (i.e., by welding, integrally forming, etc.). Accordingly, at block 312, the solution 30 is added to the tube 18. At block 316, the tube 18, with the solution 18 therein, is sealed with the cap 20. The method shown in flowchart 300 and described above is merely exemplary. There can be other methods where different blocks of the method 300 can be combined into a single block or performed simultaneously and/or the sequence of such blocks can be changed. There can also be examples where method 300 can comprise further or different blocks. Other variations can be implemented for method 300 without departing from the scope of the present disclosure.

Up to now, sample recovery and collection practices required multiple containment devices to be used in relation to a particular patient. This increased the risk of lost or mishandled individual containers of samples, and thus, would increase the chance of an incomplete analysis of the samples. However, by allowing swab-based extraction and concentration of collected material from multiple swabs, the abundance of samples that can be recovered is immense because all samples are suspended together. Then the suspended samples can be securely transported for downstream applications, such as immune and genomics applications. Additionally, the collection device shown and described herein accommodates swab-free transport and self-collection. The collection device is also inexpensive and allows collection of up to 30 μg of a specimen.

Thus, the invention provides, among other things, a sample recovery and collection devices and a kit for facilitating easy sample collection, transportation, and storage. The above-described embodiments of the invention are presented for purposes of illustration and not of limitation. Various features and advantages of the invention are set forth in the following claims.

The present invention has multiple aspects, illustrated by the following non-limiting examples.

6. Examples

Example 1

Insert Increases DNA Yield as Compared to No Insert

As discussed above, cells or tissue are collected from a subject for subsequent processing, for example, the isolation of DNA. In particular, buccal cells are often collected by a swab and then suspended in a solution contained within a tube by agitation (e.g., stirring, shaking, etc.) of the swab in the solution. The release of the buccal cells from the swab into the solution determines how much sample is available for subsequent processing. To determine if the present invention increases the isolation of buccal cells from the swab, the effectiveness of buccal cell release from the swab was examined in the absence and presence of the insert in the tube. Effectiveness of buccal cell release was determined by DNA yield from the respective samples.

Materials and Methods

Protocol without Insert (Protocol A).

Each subject did not eat, drink, smoke, or chew gum for 30 minutes before performing this protocol. Each subject received a kit including a swab pouch containing a swab and a tube containing a sample suspension solution.

The tube was removed from the kit and the cap was unscrewed from the tube to allow the swab access to the sample suspension solution in the tube. The tube was placed in a holder located within the kit to maintain the tube in an upright position and prevent loss of the sample suspension solution (e.g., tipping, spilling, etc.) while buccal cells were collected with the swab. The swab pouch was opened to expose an end of the swab opposite a swab tip to allow removal of the swab from the swab pouch and to prevent contamination of the swab tip (e.g., the subject touching the swab tip with his/her fingers). A tip of the swab was placed in the subject's mouth and the swab tip was applied against one cheek. In particular, the swab tip was rubbed against the cheek for at least 30 seconds to collect the buccal cells.

The swab tip was then removed from the subject's mouth and submerged in the sample suspension solution. The buccal cells were released from the swab tip by agitation of the swab tip in the sample suspension solution (e.g., stirring, shaking, and the like). Agitation occurred for 20 seconds. The swab tip was then removed from the sample suspension solution and the tube. The swab was discarded and the cap screwed on the tube. The tube was placed in the kit, which was sealed with adhesive tape for shipment.

Protocol with Insert (Protocol B).

Each subject did not eat, drink, smoke, or chew gum for 30 minutes before performing this protocol. Each subject received a kit including a swab pouch containing a swab and a tube. The tube contained a sample suspension solution and the insert described above.

The tube was removed from the kit and the cap was unscrewed from the tube to allow the swab access to the sample suspension solution in the tube. The tube was placed in a holder located within the kit to maintain the tube in an upright position and prevent loss of the sample suspension solution (e.g., tipping, spilling, etc.) while buccal cells were collected with the swab. The swab pouch was opened to expose an end of the swab opposite a swab tip to allow removal of the swab from the swab pouch and to prevent contamination of the swab tip (e.g., the subject touching the swab tip with his/her fingers). A tip of the swab was placed in the subject's mouth and the swab tip was applied against one cheek. In particular, the swab tip was rubbed against the cheek for at least 30 seconds to collect the buccal cells.

The swab tip was then removed from the subject's mouth and inserted into the tube and through the insert located within the tube by a downward twisting (e.g., screw-like) motion. Light force was required in the application of the twisting motion given the resistance afforded by the insert.

Once the swab tip was located beneath the insert and submerged in the sample suspension solution, the swab tip was shaken by moving the swap tip up and down while maintaining the swab tip below the insert (i.e., the swab tip was not moved beyond the insert during the upward motion). Shaking occurred for 20 seconds. The swab, and thus the swab tip, were moved through the insert and removed from the tube by an upwards twisting motion (e.g., unscrew-like motion or motion opposite that used for insertion of the swab tip into the tube). The swab was discarded and the cap screwed on the tube. The tube was placed in the kit, which was sealed with adhesive tape for shipment.

Sample Collection.

Puritan-Cotton (PC) swabs were used to collect the buccal cell samples and samples were collected in duplicate from thirty subjects. A two day interval occurred between each collection. In each collection, each subject provided two samples, in which one sample was obtained by following protocol A (i.e., no insert was present in the tube) and the other sample was obtained by following protocol B (i.e., the insert was present in the tube). All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. DNA was extracted from each sample with the DNeasy kit (Qiagen, Valencia, Calif., USA). DNA yield was determined by three separate methods, namely by absorbance of ultraviolet (UV) light with a Nano-Drop instrument (Thermo Scientific, Wilmington, Del., USA), fluorescence with PICOGREEN dsDNA quantitation assay (Life Technologies, Carlsbad, Calif., USA), and quantitative amplification of the human beta actin gene.

Results

Table 1 shows the median DNA yield obtained from buccal cell samples that were collected by protocols A and B (i.e., absence and presence of the insert in the tube, respectively). When the insert was absent from the tube, the median DNA yield was 1.4 µg/mL (standard deviation was 1.2). However, when the insert was present in the tube, the median DNA yield was 8.1 µg/mL (standard deviation was 2.9). These data indicated that inclusion of the insert in the tube provided a 5.8-fold increase in DNA yield from buccal cell samples as compared to absence of the insert in the tube. Because the DNA was obtained from all samples by the same method, this increased DNA yield indicated that more buccal cells were isolated from the swab tip when the insert was present in the tube as compared to when the insert was absent from the tube.

The insert by applying a squeezing force upon the swab tip (i.e., during insertion and removal of the swab tip from the tube) more effectively released buccal cells from the swab tip into the sample suspension solution than simple agitation (e.g., stirring) of the swab tip in the sample suspension solution. Such increased isolation of buccal cells from the swab in turn provided more sample for processing, i.e., increased DNA yield. Accordingly, the presence of the insert provided more efficient isolation of buccal cells from a swab tip and thus more buccal cells for sample processing from a single swab tip.

TABLE 1

|  | DNA Yield (µg/mL) without Insert (Protocol A) | DNA Yield (µg/mL) with Insert (Protocol B) |
| --- | --- | --- |
| Median | 1.4 | 8.1 |
| Standard Deviation | 1.2 | 2.9 |

*Data in Table 1 reflected all three methods of DNA quantitation, namely quantitation with the Nanodrop instrument, PICOGREEN assay, and quantitative polymerase chain reaction (PCR).

Example 2

Concentration of the Buccal Cell Sample with the Insert

The insert increased the isolation of buccal cells from the swab tip, thereby providing from a single swab, more sample for subsequent processing (e.g., DNA isolation) as compared to when the insert was absent. To determine if the insert can facilitate concentration of buccal cells collected from a subject, buccal cells were collected with one, two, three, or four swabs per subject and the concentration of buccal cells in the respective sample suspension solutions was indirectly measured by DNA yield from the respective samples.

Materials and Methods

Protocol with 1 Swab.

The subject did not eat, drink, smoke, or chew gum for 30 minutes before performing this protocol. The subject received a kit including a swab pouch containing a swab and a tube. The tube contained a sample suspension solution and the insert described above.

The tube was removed from the kit and the cap was unscrewed from the tube to allow the swab access to the sample suspension solution in the tube. The tube was placed in a holder located within the kit to maintain the tube in an upright position and prevent loss of the sample suspension solution (e.g., tipping, spilling, etc.) while buccal cells were collected with the swab. The swab pouch was opened to expose an end of the swab opposite a swab tip to allow removal of the swab from the swab pouch and to prevent contamination of the swab tip (e.g., the subject touching the swab tip with his/her fingers). A tip of the swab was placed in the subject's mouth and the swab tip was applied against one cheek. In particular, the swab tip was rubbed against the cheek for at least 30 seconds to collect the buccal cells.

The swab tip was then removed from the subject's mouth and inserted into the tube and through the insert located within the tube by a downward twisting (e.g., screw-like) motion. Light force was required in the application of the twisting motion given the resistance afforded by the insert.

Once the swab tip was located beneath the insert and submerged in the sample suspension solution, the swab tip was shaken by moving the swap tip up and down while maintaining the swab tip below the insert (i.e., the swab tip was not moved beyond the insert during the upward motion). Shaking occurred for 20 seconds. The swab, and thus the swab tip, were moved through the insert and removed from the tube by an upwards twisting motion (e.g., unscrew-like motion or motion opposite that used for insertion of the swab tip into the tube). The swab was discarded and the cap screwed on the tube. The tube was placed in the kit, which was sealed with adhesive tape for shipment. Accordingly, the protocol with 1 swab isolated buccal cells from one swab with a single tube (and thus insert).

Protocol with 2 Swabs.

This protocol was the same as the protocol with 1 swab described above with the following modifications. The kit instead included two swab pouches and two swabs. The first swab was used to collect and then release buccal cells into the sample suspension solution as described above in the protocol with 1 swab.

After disposal of the first swab, a second swab pouch was opened to expose an end of the second swab opposite a second swab tip to allow removal of the second swab from the second swab pouch and to prevent contamination of the second swab tip (e.g., the subject touching the second swab tip with his/her fingers). The second swab tip was placed in the subject's mouth and the second swab tip was applied against one cheek. In particular, the second swab tip was rubbed against the cheek for at least 30 seconds to collect the buccal cells. The second swab tip was then removed from the subject's mouth and inserted into the tube (i.e., the same tube used for the first swab) and through the insert located within the tube by a downward twisting (e.g., screw-like) motion. Light force was required in the application of the twisting motion given the resistance afforded by the insert.

Once the second swab tip was located beneath the insert and submerged in the sample suspension solution, the second swab tip was shaken by moving the second swab tip up and down while maintaining the second swab tip below the insert (i.e., the second swab tip was not moved beyond the insert during the upward motion). Shaking occurred for 20 seconds. The second swab, and thus the second swab tip, were moved through the insert and removed from the tube by an upwards twisting motion (e.g., unscrew-like motion or motion opposite that used for insertion of the second swab tip into the tube). The second swab was discarded and the cap screwed on the tube. The tube was placed in the kit, which was sealed with adhesive tape for shipment. Accordingly, the protocol with 2 swabs isolated buccal cells from two separate swabs with a single tube (and thus insert).

Protocol with 3 Swabs.

This protocol was the same as the protocol with 2 swabs described above with the following modifications. The kit instead included three swab pouches and three swabs. The first and second swabs were used to collect and then release buccal cells into the sample suspension solution as described above in the protocol with 2 swabs.

After disposal of the second swab, a third swab pouch was opened to expose an end of the third swab opposite a third swab tip to allow removal of the third swab from the third swab pouch and to prevent contamination of the third swab tip (e.g., the subject touching the third swab tip with his/her fingers). The third swab tip was placed in the subject's mouth and the third swab tip was applied against one cheek. In particular, the third swab tip was rubbed against the cheek for at least 30 seconds to collect the buccal cells. The third swab tip was then removed from the subject's mouth and inserted into the tube (i.e., the same tube used for the first and second swabs) and through the insert located within the tube by a downward twisting (e.g., screw-like) motion. Light force was required in the application of the twisting motion given the resistance afforded by the insert.

Once the third swab tip was located beneath the insert and submerged in the sample suspension solution, the third swab tip was shaken by moving the third swab tip up and down while maintaining the third swab tip below the insert (i.e., the third swab tip was not moved beyond the insert during the upward motion). Shaking occurred for 20 seconds. The third swab, and thus the third swab tip, were moved through the insert and removed from the tube by an upwards twisting motion (e.g., unscrew-like motion or motion opposite that used for insertion of the third swab tip into the tube). The third swab was discarded and the cap screwed on the tube. The tube was placed in the kit, which was sealed with adhesive tape for shipment. Accordingly, the protocol with 3 swabs isolated buccal cells from three separate swabs with a single tube (and thus insert).

Protocol with 4 Swabs.

This protocol was the same as the protocol with 3 swabs described above with the following modifications. The kit instead included four swab pouches and four swabs. The first, second, and third swabs were used to collect and then release buccal cells into the sample suspension solution as described above in the protocol with 3 swabs.

After disposal of the third swab, a fourth swab pouch was opened to expose an end of the fourth swab opposite a fourth swab tip to allow removal of the fourth swab from the fourth swab pouch and to prevent contamination of the fourth swab tip (e.g., the subject touching the fourth swab tip with his/her fingers). The fourth swab tip was placed in the subject's mouth and the fourth swab tip was applied against one cheek. In particular, the fourth swab tip was rubbed against the cheek for at least 30 seconds to collect the buccal cells. The fourth swab tip was then removed from the subject's mouth and inserted into the tube (i.e., the same tube used for the first, second, and third swabs) and through the insert located within the tube by a downward twisting (e.g., screw-like) motion. Light force was required in the application of the twisting motion given the resistance afforded by the insert.

Once the fourth swab tip was located beneath the insert and submerged in the sample suspension solution, the fourth swab tip was shaken by moving the fourth swab tip up and down while maintaining the fourth swab tip below the insert (i.e., the fourth swab tip was not moved beyond the insert during the upward motion). Shaking occurred for 20 seconds. The fourth swab, and thus the fourth swab tip, were moved through the insert and removed from the tube by an upwards twisting motion (e.g., unscrew-like motion or motion opposite that used for insertion of the fourth swab tip into the tube). The fourth swab was discarded and the cap screwed on the tube. The tube was placed in the kit, which was sealed with adhesive tape for shipment. Accordingly, the protocol with 4 swabs isolated buccal cells from four separate swabs with a single tube (and thus insert).

Sample Collection.

Puritan-Cotton (PC) swabs were used to collect the buccal cell samples in triplicate from a single subject. A two day interval occurred between each collection. In each collection, the subject provided four samples. The first, second, third, and fourth samples each contained buccal cells in sample suspension solution, in which the buccal cells were collected with one, two, three, and four swabs, respectively, as described in the protocols above. The use of four swabs for the collection of a single sample was considered a maximum collection in accordance with the National Bone Marrow Registry Sample collection guidelines and input from the subject. All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. DNA was extracted from each sample with the DNeasy kit (Qiagen, Valencia, Calif., USA). DNA yield was determined by three separate methods, namely by absorbance of ultraviolet (UV) light with a Nano-Drop instrument (Thermo Scientific, Wilmington, Del., USA), fluorescence with PICOGREEN dsDNA quantitation assay (Life Technologies, Carlsbad, Calif., USA), and quantitative amplification of the human beta actin gene.

Results

Table 2 shows the median DNA yield obtained from buccal cell samples that were collected with one, two, three, or four swabs. The median DNA yield from buccal cell samples collected with one swab, two swab, three swabs, and four swabs was 6.9 µg/mL, 12.0 µg/mL, 18.8 µg/mL, and 25.3 µg/mL, respectively. These data indicated that DNA yield increased as the number of swabs used to collect buccal cells increased. Because the DNA was obtained from all samples by the same method, a larger DNA yield reflected a larger amount of buccal cells in the sample suspension solution. The volume of the sample suspension solution was uniform across the samples and thus, a larger DNA yield also reflected a higher concentration of buccal cells in the sample suspension solution. Accordingly, these data indicated that the concentration of buccal cells in the sample suspension solution increased with the number of swabs used to collect the buccal cells. These data demonstrated that the insert can be used with multiple swabs in a single collection to increase the concentration of buccal cells in the sample suspension solution.

TABLE 2

|  | DNA Yield with 1 Swab | DNA Yield with 2 Swabs | DNA Yield with 3 Swabs | DNA Yield with 4 Swabs |
|---|---|---|---|---|
| Median | 6.9 | 12.0 | 18.8 | 25.3 |
| Standard Deviation | 1.9 | 2.0 | 2.9 | 4.4 |

*The units for DNA yield are µg/mL.
**Data in Table 2 reflected all three methods of DNA quantitation, namely quantitation with the Nanodrop instrument, PICOGREEN assay, and quantitative PCR.

Example 3

Efficiency of Cell Release is Unaffected by the Swab Material

As described above, inclusion of the insert in the tube increased the efficiency of releasing buccal cells from the swab. To determine if the material comprising the swab affected the efficiency of buccal cell isolation with the insert, three different swab materials were examined, namely polyester, dacron, and cotton. In particular, Copan-Genomic (COP-Polyester), Puritan-Hydra (P-Dacron), and Puritan-Cotton (PC) were used in collecting the buccal cells as described in more detail below.

Materials and Methods

Modified Protocol with 4 Swabs.

Buccal cells were collected from the subject as described in Example 2, following the protocol with 4 swabs, with the following modification: prior to discarding each swab, each swab was processed as described in the DNeasy kit (Qiagen, Valencia, Calif., USA) protocol for extracting DNA from buccal swabs, to isolate any buccal cells remaining on the swab (i.e., a post-suspension sample). This post-suspension sample served as a control, which indicated the amount of buccal cells remaining on the swab tip after removal of the swab tip from the insert and tube.

Sample Collection.

Copan-Genomic (COP-Polyster), Puritan-Hydra (P-Dacron), and Puritan-Cotton (PC) swabs were used to collect buccal cell samples in triplicate from 192 subjects. A two day interval occurred between each collection. In each collection, each subject provided three samples. The first, second, and third samples used four swabs of COP-Polyster, P-Dacron, and PC, respectively, to collect the buccal cells from each subject. In other words, at each collection, buccal cells were collected with three different swabs for each type of swab material (i.e., 4 swabs of COP-Polyester, 4 swabs of P-Dacron, and 4 swabs of PC). All suspension and post-suspension samples were processed, stored, and transported at room temperature. Transport occurred by standard United States Postal Service mailing process.

Sample Processing.

To avoid bias in sample processing, each suspension and post-suspension sample was divided into two equal volumes with each volume being sent to a different accredited service lab. DNA was extracted from each sample with the DNeasy kit (Qiagen, Valencia, Calif., USA). DNA yield was determined by three separate methods, namely by absorbance of ultraviolet (UV) light with a NanoDrop instrument (Thermo Scientific, Wilmington, Del., USA), fluorescence with PICOGREEN dsDNA quantitation assay (Life Technologies, Carlsbad, Calif., USA), and by quantitative amplification of the human beta actin gene.

Results

Table 3 shows the median DNA yield obtained from the suspension and post-suspension samples for each of the COP-Polyester, P-Dacron, and PC swab materials. DNA was extracted from the suspension and post-suspension samples in the same manner as described above.

DNA was not detectable in the post-suspension sample when the swab material was P-Dacron. This data indicated that about 100% of the buccal cells were transferred from the P-Dacron swab tip to the sample suspension solution because no (or very little) buccal cells remained on the P-Dacron swab tip after removal from the insert and tube for DNA extraction. Insignificant amounts of DNA were detected in the post-suspension sample when the swab material was either PC or COP-Polyester. For PC and COP-Polyester, about 0.2% and 0.07% of the total DNA yield was obtained from the post-suspension solution. These data indicated that about 99.8% or greater of the total DNA yield was obtained from the sample suspension solution, which in turn, indicated that the buccal cells were efficiently transferred from the swab to the sample suspension solution in the tube because little to no DNA was obtained from the post-suspension sample. Accordingly, these data also indicated that about 100% of the buccal cells were efficiently released from the swab into the sample suspension solution in the tube regardless of the swab material. In summary, the squeezing force applied by the insert to the swab did not differentiate between swab material in affecting release of the buccal cells from the swab into the sample suspension solution in the tube. Accordingly, by causing efficient transfer of the buccal cells from the swab tip to the sample suspension solution, loss of the buccal cells was minimized and more sample was available for subsequent processing.

TABLE 3

|  | P-Dacron | | PC | | COP-Polyester | |
|---|---|---|---|---|---|---|
|  | Suspension (total DNA) | Post-Suspension (total DNA) | Suspension (total DNA) | Post-Suspension (total DNA) | Suspension (total DNA) | Post-Suspension (total DNA) |
| Median | 24.7 | ND | 21.3 | 0.05 | 14.7 | 0.01 |
| St. Dev. | 3.8 |  | 3.4 | 0.001 | 1.5 | 0.003 |

*St. Dev = Standard Deviation
**ND = Not Detectable
***Total DNA values are the total DNA in micrograms extracted from the respective 1 mL of sample.
****Data in Table 3 reflected all three methods of DNA quantitation, namely quantitation with the Nanodrop instrument, PICOGREEN assay, and quantitative PCR.

Example 4

RNA Yield with Different Swab Materials

As shown above, the isolation of buccal cells and thus DNA yield were significantly improved when the insert was used to release buccal cells from the swab. Additionally, the swab materials COP-Polyster, P-Dacron, and PC were used with the insert for buccal cell isolation, in which DNA was subsequently extracted from the isolated buccal cells. To further examine buccal cell isolation with the insert, it was determined if RNA could be extracted from the isolated buccal cells.

Materials and Methods

Protocol with 4 Swabs.

Buccal cells were collected from the subject as described in Example 2, following the protocol with 4 swabs.

Sample Collection.

Copan-Genomic (COP-Polyster), Puritan-Hydra (P-Dacron), and Puritan-Cotton (PC) swabs were used to collect buccal cell samples in triplicate from a single subject. A two day interval occurred between each collection. In each collection, the subject provided three samples. The first, second, and third samples used four swabs of COP-Polyester, P-Dacron, and PC, respectively, to collect the buccal cells from the subject. In other words, at each collection, buccal cells were collected with three different swabs for each type of swab material (i.e., 4 swabs of COP-Polyester, 4 swabs of P-Dacron, and 4 swabs of PC). All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. RNA was extracted from each sample with the RNeasy kit (Qiagen, Valencia, Calif., USA). RNA yield was determined with a Ripogreen RNA assay (Life Technologies, Carlsbad, Calif., USA).

Results

Figure 12:
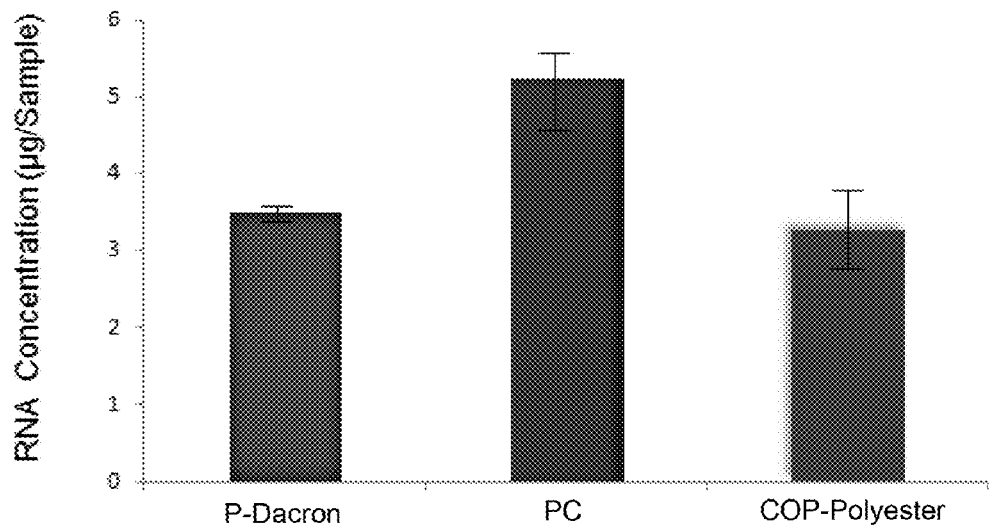
FIG. 12 shows a graph plotting swab material vs. RNA yield.

As shown in FIG. 12, RNA was extracted from the buccal cells when the insert was used in the removal of the buccal cells from the swab tip. The error bars in FIG. 12 represent the standard deviation. The RNA was extracted from buccal cells collected with swabs having the swab materials P-Dacron, PC, or COP-Polyester. Accordingly, these data indicated that RNA was obtained from the buccal cells, which were isolated in combination with the insert, regardless of whether the swab material was P-Dacron, PC, or COP-Polyester.

Example 5

Bacterial Contamination of Extracted DNA

As discussed above, RNA and DNA were extracted from buccal cells that were isolated in combination with the insert. To determine if bacterial nucleic acids contaminated the extracted DNA, primers specific for the 16S ribosomal gene were employed to examine the level of bacterial nucleic acid contamination.

Materials and Methods

Protocol with 4 Swabs.

Buccal cells were collected from each subject as described in Example 2, following the protocol with 4 swabs.

Sample Collection.

Copan-Genomic (COP-Polyster), Puritan-Hydra (P-Dacron), and Puritan-Cotton (PC) swabs were used to collect buccal cell samples in triplicate from 24 subjects. A two day interval occurred between each collection. In each collection, each subject provided three samples. The first, second, and third samples used four swabs of COP-Polyester, P-Dacron, and PC, respectively, to collect the buccal cells from each subject. In other words, at each collection, buccal cells were collected with three different swabs for each type of swab material (i.e., 4 swabs of COP-Polyester, 4 swabs of P-Dacron, and 4 swabs of PC). All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. DNA was extracted from each sample with the DNeasy kit (Qiagen, Valencia, Calif., USA).

Amplification of the 16S Ribosomal RNA (rRNA) Gene.

The DNA extracted from the respective buccal cells samples was used as a template in a polymerase chain reaction (PCR). The primers were specific for the 16S rRNA gene, which is found in prokaryotes (e.g., bacteria), but not eukaryotes (e.g., humans). The presence and amount of bacterial DNA was determined by comparison to positive controls.

Results

Figure 13:
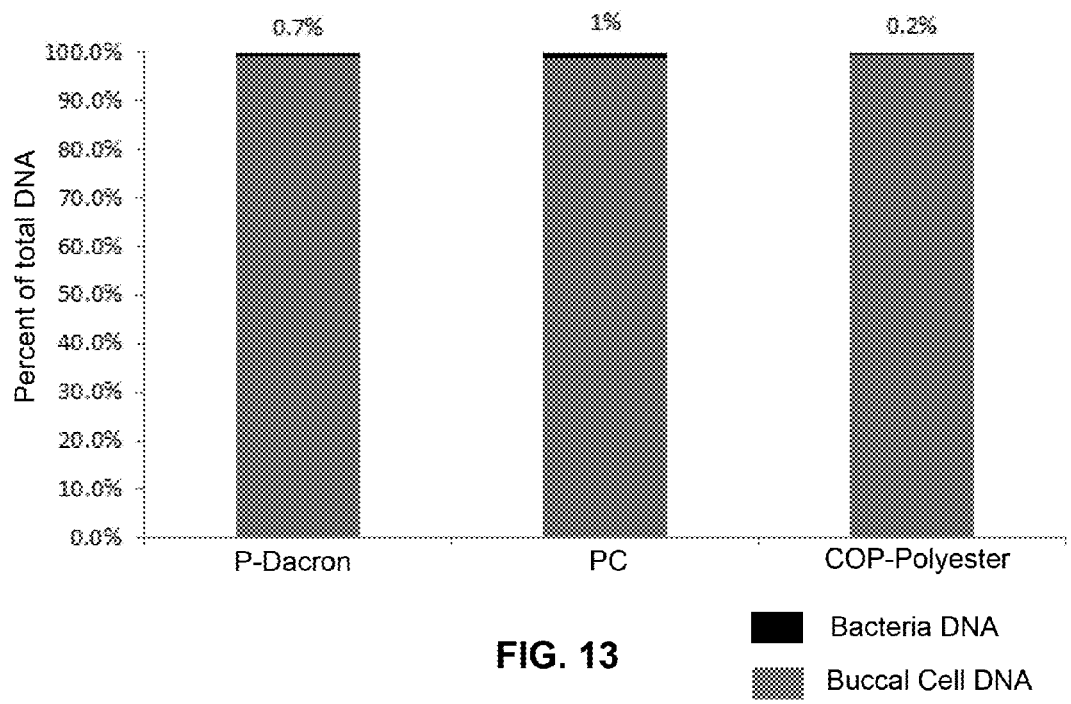
FIG. 13 shows a graph plotting swab material vs. percent of total DNA.

As shown in FIG. 13, 1% or less of the total DNA extracted from the buccal cell sample was attributed to bacterial genomic DNA. The level of bacterial genomic DNA was measured by whether the 16S rRNA gene was amplified from the DNA extracted from respective buccal cell samples. For each bar in FIG. 13, black represents bacterial DNA and grey represents buccal cell DNA (i.e., the subject's DNA). Additionally, bacterial nucleic acid contamination was 0.7 percent, 1 percent, and 0.2 percent for the swab materials P-Dacron, PC, and COP-Polyester, respectively. These data indicated that little bacterial contamination of the buccal cell sample occurred during collection of the buccal cells with the swab materials P-Dacron, PC, and COP-Polyester. These data also indicated that little bacterial contamination occurred during removal of the cells from the swab tip. These data further indicated that 99% or greater of the extracted DNA was not bacterial DNA and thus was usable for downstream applications. Accordingly, these and the above data indicated that the insert provided increased DNA yield (relative to absence of the insert), efficiently removed buccal cells from the swab tip (about 100% removal), was compatible with multiple swab materials, facilitated RNA extraction, and did not result in significant bacterial contamination of the buccal cell sample.

Example 6

Stability of the Buccal Cell Sample

As discussed above, the insert increased the DNA yield by providing more efficient isolation of the buccal cells from the swab tip into the sample suspension solution. Subsequently, the sample suspension solution, and thus the buccal cell sample, is transported for further processing (e.g., DNA extraction). Transportation often takes time and thus it is required to store buccal cell samples. Additionally, buccal cell samples may need to be stored for a period of time before further processing occurs. Accordingly, to examine the stability of the buccal cell sample, buccal cell samples were incubated for different periods of time and DNA was then extracted after incubation. The quality of the extracted DNA served as an indicator of the stability of the respective buccal cell sample. The quality of the DNA was determined by examining whether the extracted DNA was intact as described in more detail below.

Materials and Methods

Protocol with 4 Swabs.

Buccal cells were collected from the subject as described in Example 2, following the protocol with 4 swabs.

Sample Collection.

Puritan-Cotton (PC) swabs were used to collect buccal cell samples in triplicate from a single subject. A four hour interval occurred between each collection. All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. DNA was extracted from each sample with the DNeasy kit (Qiagen, Valencia, Calif., USA). DNA extraction occurred at day 0, day 180, and day 360 after collection of the buccal cell sample. Until DNA extraction occurred, buccal cell samples were stored in their respective tubes at room temperature.

Restriction Enzyme Digestion.

Extracted DNA was digested with EcoRI.

Electrophoresis.

Figure 14:
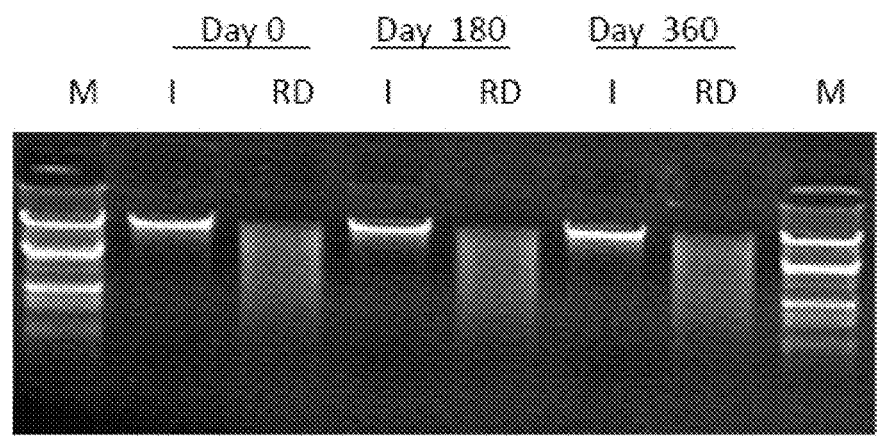
FIG. 14 shows an image of an agarose gel stained with ethidium bromide. M is the marker, I is undigested extracted DNA, and RD is digested extracted DNA.

Extracted DNA and extracted DNA digested with EcoRI were analyzed by gel electrophoresis, namely a 1.0% agarose gel. 5 µL of each DNA was loaded in its respective lane depicted in FIG. 14. The marker was lambda DNA digested with HindIII and EcoRI.

Results

FIG. 14 shows the electrophoretic analysis of DNA extracted from buccal cell samples incubated at room temperature for 180 days or 360 days in respective tubes. Day 0 is DNA extracted from the buccal cells on the same day as collection of the buccal cells. At day 0, day 180, and day 360, the extracted DNA was intact, yet was susceptible to EcoRI digestion ("RD" in FIG. 14 indicated DNA digested with EcoRI while "I" indicated DNA that was not digested with EcoRI). No difference was observed between the DNA extracted from buccal cell samples on day 0, day 180, and day 360. Accordingly, these data indicated that the buccal cells were stable in the sample suspension solution at room temperature from the time of collection (i.e., day 0) through an extended period time (i.e., at least 360 days) because intact DNA was obtained from these buccal cells at day 0, day 180, and day 360.

Example 7

Use of Extracted DNA in the Polymerase Chain Reaction (PCR)

As discussed above, the insert increased the DNA yield by providing more efficient isolation of the buccal cells from the swab tip into the sample suspension solution. Extracted DNA is used in many different applications, for example, the polymerase chain reaction. To determine whether the DNA extracted from buccal cells isolated in combination with the insert could be used in downstream applications, the extracted DNA was used as a template for the amplification of the human beta actin gene.

Materials and Methods

Protocol with 4 Swabs.

Buccal cells were collected from the subject as described in Example 2, following the protocol with 4 swabs.

Sample Collection.

Puritan-Cotton (PC) swabs were used to collect buccal cell samples in triplicate from a single subject. A four hour interval occurred between each collection. All samples were processed, stored, and transported at room temperature. Transport occurred by standard United States Postal Service mailing process.

Sample Processing.

To avoid bias in sample processing, each sample was divided into two equal volumes with each volume being sent to a different accredited service lab. DNA was extracted from each sample with the DNeasy kit (Qiagen, Valencia, Calif., USA).

Amplification of the Human Beta Actin Gene.

The DNA extracted from the respective buccal cell samples was used as a template in PCR. The primers were specific for the human beta actin gene and resulted in an amplicon of 300 base pair (bp). 24 replicates were performed along with a negative control, which contained no DNA.

Electrophoresis.

Amplicons were analyzed by agarose gel electrophoresis, namely with a 4% agarose gel. 5 µL of DNA was loaded in each lane and the marker (M) was a 25 bp ladder.

Results

Figure 15:
FIG. 15 shows an image of an agarose gel stained with ethidium bromide. The lanes are numbered consecutively and corresponded to the 24 replicates. The flanking lanes included the negative control (NC) and the marker (M).

FIG. 15 shows the electrophoretic analysis of the amplicons. Each of the 24 replicates yielded the expected 300 bp amplicon and no other amplicons. These data indicated that the extracted DNA served as a template in an amplification reaction for the generation of a specific amplicon. Accordingly, amplification (or PCR) was not inhibited by how the buccal cells were collected, isolated, and stored because the DNA extracted from these buccal cells served as a template in the amplification reaction, which yielded the expected amplicon.

Example 8

Comparison of Buccal Swab- and Insert-Based Methods

As described above in Example 1, inclusion of the insert in the tube significantly increased DNA yield by more efficiently isolating buccal cells from the swab tip. Other methods exist for buccal cell collection such as the use of the following buccal swabs: Dacron/paper swab, foam swab, and Isohelix T-swab. Accordingly, the efficiency of buccal cell isolation as measured by DNA yield was examined for a method using a buccal swab and a method using the insert.

Materials and Methods

Protocol with the Insert.

Buccal cells were collected from the subject as described in Example 2, following the protocol with 4 swabs. Puritan-Cotton (PC) swabs were used to collect the buccal cells from the subject.

Protocol with a Dacron/Paper Swab, a Foam Swab, or an Isohelix T-Swab.

The subject did not eat, drink, smoke, or chew gum for 30 minutes before performing this protocol. The subject received a dacron/paper swab, a foam swab, or an isohelix-T swab. A tip of the swab was placed in the subject's mouth and the swab tip was applied against one cheek. In particular, the swab tip was rubbed against the cheek for 60 seconds to collect the buccal cells. The swab tip was then removed from the subject's mouth and dried.

Sample Collection.

Buccal cells were collected from six subjects using the above protocols. One day occurred in between each collection with the different swabs. All samples were processed and stored at room temperature.

Sample Processing.

DNA was extracted from each sample with the DNeasy kit (Qiagen, Valencia, Calif., USA). DNA yield was determined by absorbance of ultraviolet (UV) light with a NanoDrop instrument (Thermo Scientific, Wilmington, Del., USA).

Results

Figure 16:
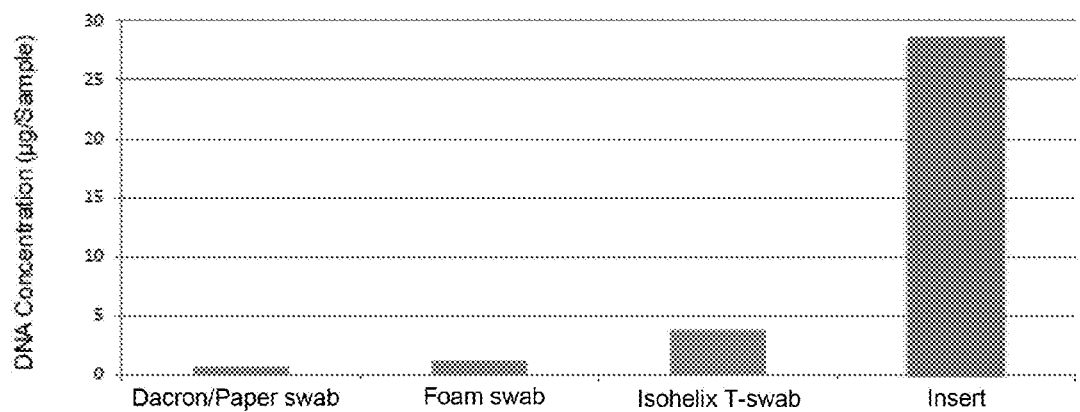
FIG. 16 shows a graph plotting collection method vs. DNA yield.

FIG. 16 shows the DNA yield for a method using a buccal swab (i.e., Dacron/paper swab, foam swab, or isohelix T-swab) and a method using the insert. DNA yield was significantly higher for the method using the insert as compared to the method using the buccal swab. The method with the insert provided a more than 20-fold increase in DNA yield as compared to the method using the buccal swab. Accordingly, these data indicated that the method using the insert more efficiently isolated buccal cells, thereby providing a larger amount of sample for subsequent processing and analysis.

Example 9

Comparison of Saliva- and Insert-Based Methods

A method employing the insert more efficiently isolated buccal cells, and thus provided increased DNA yield, as compared to a method utilizing a buccal swab as described above in Example 8. Besides buccal cells, other types of samples that can be collected from the subject include, for example, salvia. One method for collecting a saliva sample is with Oragene DNA (OG 500).

Materials and Methods

Protocol with Insert.

Buccal cells were collected from the subject as described in Example 2, following the protocol with 4 swabs. Copan-Genomic (COP-Polyster), Puritan-Hydra (P-Dacron), and Puritan-Cotton (PC) swabs were used to collect buccal cell samples in triplicate from 192 subjects. A two day interval occurred between each collection. In each collection, each subject provided three samples. The first, second, and third samples used four swabs of COP-Polyster, P-Dacron, and PC, respectively, to collect the buccal cells from each subject. In other words, at each collection, buccal cells were collected with three different swabs for each type of swab material (i.e., 4 swabs of COP-Polyster, 4 swabs of P-Dacron, and 4 swabs of PC). All samples were processed, stored, and transported at room temperature. Transport occurred by standard United States Postal Service mailing process.

To avoid bias in sample processing, each sample was divided into two equal volumes with each volume being sent to a different accredited service lab. DNA was extracted from each sample with the DNeasy kit (Qiagen, Valencia, Calif., USA). DNA yield was determined by three separate methods, namely by absorbance of ultraviolet (UV) light with a Nano-Drop instrument (Thermo Scientific, Wilmington, Del., USA), fluorescence with PICOGREEN dsDNA quantitation assay (Life Technologies, Carlsbad, Calif., USA), and by quantitative amplification of the human beta actin gene.

Protocol with Oragene DNA (OG 500).

The manufacturer's instructions provided with OG 500 were followed. Saliva samples were collected from 24 subjects. All samples were processed and stored at room temperature. DNA was extracted from 1 mL of each sample.

Results

Figure 17:
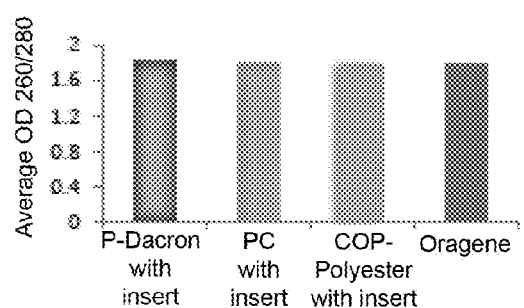
FIG. 17 shows a graph plotting collection method vs. average OD 260/280.
Figure 18:
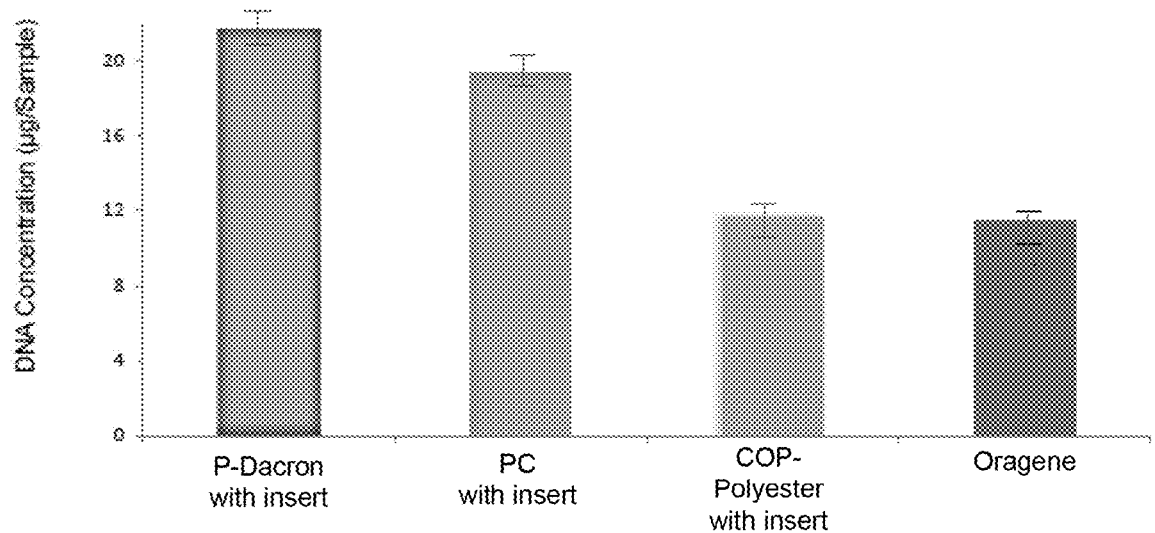
FIG. 18 shows a graph plotting collection method vs. DNA yield.

FIGS. 17 and 18 show the average A260/A280 ratio and DNA yield obtained from the method using the insert and the method using Oragene. The data in FIG. 18 are representative of DNA yield as measured with the NanoDrop instrument described above and the error bars reflected standard deviation. As observed above in Example 3, the DNA was extracted from the buccal cell samples when the insert was used in combination with the swab materials P-Dacron, PC, and COP-Polyester. Regardless of which swab material was used in combination with the insert, the resulting DNA yield was greater than 50 ng/μL. Similar A260/A280 ratios were observed for the DNA extracted from the saliva samples (i.e., Oragene method) and the buccal cell samples (i.e., method with insert in combination with the swab materials P-Dacron, PC, or COP-Polyester). Additionally, the method using Oragene yielded at least as much DNA as the method using the insert in combination with swab material COP-Polyester. The method using Oragene yielded less DNA than the method using the insert in combination with swab material P-Dacron or PC. Accordingly, these data indicated that sample collection by the Oragene method resulted in DNA quality similar to the DNA quality obtained from buccal cells collected with the insert method. These data also indicated that sample collection by the Oragene method resulted in DNA yields that were less than or similar to the DNA yields obtained from buccal cells collected with the insert method.

Example 10

Bacterial Contamination in Different Sample Collection Methods

As discussed above in Example 5, sample collection with the insert resulted in little contamination of extracted DNA with bacterial DNA (i.e., 1% or less of the total DNA was bacterial DNA). To further examine contaminating bacterial DNA, sample collection with the insert was compared to other sample collection methods, for example, venous blood collection, buccal cell collection with buccal swabs, and salvia collection with Oragene DNA (OG 500).

Materials and Methods

Protocol with Insert.

Buccal cells were collected from the subject as described in Example 2, following the protocol with 4 swabs. Puritan-Cotton (PC) swabs were used to collect buccal cell samples in triplicate from a single subject. A two-day interval occurred between each collection. All samples were processed, stored, and transported at room temperature. Transport occurred by standard United States Postal Service mailing process.

Protocol with Oragene DNA (OG 500).

The manufacturer's instructions provided with OG 500 were followed. Saliva samples were collected from 24 subjects. All samples were processed and stored at room temperature. DNA was extracted from 1 mL of each sample.

Protocol with Venous Blood.

A venous blood sample was collected from the subject using sterile technique.

Protocol with Buccal Swab.

The subject did not eat, drink, smoke, or chew gum for 30 minutes before performing this protocol. A PC swab was used to collect buccal cells from the subject. In particular, a tip of the swab was placed in the subject's mouth and the swab tip was applied against one cheek. In particular, the swab tip was rubbed against the cheek for 60 seconds to collect the buccal cells. The swab tip was then removed from the subject's mouth and dried.

Protocol with Mouth Wash.

Mouthwash rinse was employed to collect buccal cells from the subject. About 1 hour after teeth brushing, 10 mL of undiluted commercial mouthwash was vigorously swished in the subject's mouth for 60 seconds to collect buccal cells. The mouthwash was then expelled into a collection container. The sample was processed and stored at room temperature.

Sample Processing.

To avoid bias in sample processing, each sample obtained by the above protocols was divided into two equal volumes with each volume being sent to a different accredited service lab. DNA was extracted from each sample with the DNeasy kit (Qiagen, Valencia, Calif., USA).

Amplification of the 16S Ribosomal RNA (rRNA) Gene.

The DNA extracted from the respective samples was used as a template in a polymerase chain reaction (PCR). The primers were specific for the 16S rRNA gene, which is found in prokaryotes (e.g., bacteria), but not eukaryotes (e.g., humans). The presence and amount of bacterial DNA was determined by comparison to positive controls.

Results

Figure 19:
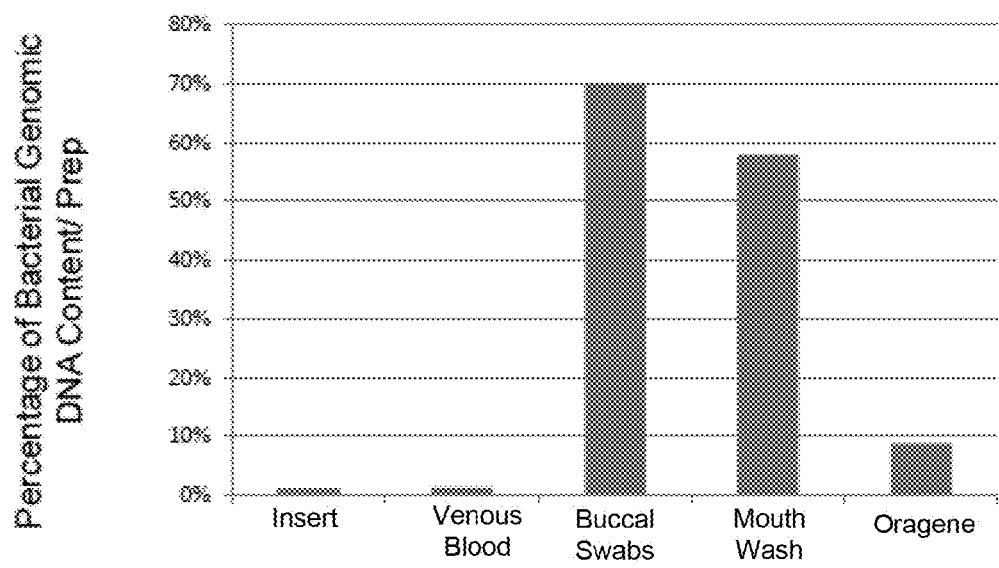
FIG. 19 shows a graph plotting collection method vs. percent bacterial DNA per prep.

FIG. 19 shows the amount of bacterial DNA detected in the DNA extracted from respective samples. As observed above in Example 5, less than 1% of extracted DNA comprised bacterial DNA when the DNA was extracted from buccal cells collected with a method using the insert. A similar amount of contamination was observed for DNA extracted from venous blood. The collection of saliva via the Oragene method resulted in higher contamination. Nearly 10% of the DNA extracted from the saliva collected by the Oragene method comprised bacterial DNA. Even higher amounts of bacterial DNA contamination (about 70% contamination) were observed in the DNA extracted from samples collected with buccal swabs. As a control, DNA extracted from buccal cells collected via mouthwash resulted in about 60% of extracted DNA comprising bacterial DNA. Accordingly, these data indicated that the insert did not result in significant contamination of the buccal cell sample. Sample collection with the insert achieved significantly lower bacterial contamination (as measured by contaminating bacterial DNA) as compared to buccal cell collection with buccal swabs and mouthwash, and saliva collection with Oragene. Venous blood was collected in a sterile manner and achieved similar levels of bacterial contamination as sample collection with the insert. In other words, sample collection with the insert provided levels of bacterial contamination comparable to samples collected in a sterile manner.

Example 11

Subject Compliance with Different Sample Collection Methods

As described above, sample collection with the insert resulted in comparable or higher DNA yields as compared to other sample collection methods. Sample collection with the insert also resulted in lower bacterial contamination as compared to other sample collection methods. To further compare sample collection with the insert to other sample collection methods, compliance of the subject was examined as described below.

Materials and Methods

Data Collection.

The response of 100 volunteers (per collection) in reporting to a designated lab location for submission of invasive (e.g., venous blood collection as described above in Example 10) and non-invasive (e.g., saliva and buccal cell collection). Saliva collection was done with Oragene as described in Examples 9 and 10. Buccal cell collection with the insert was done as described in Example 5 (with 4 swabs).

Results

Figure 20:
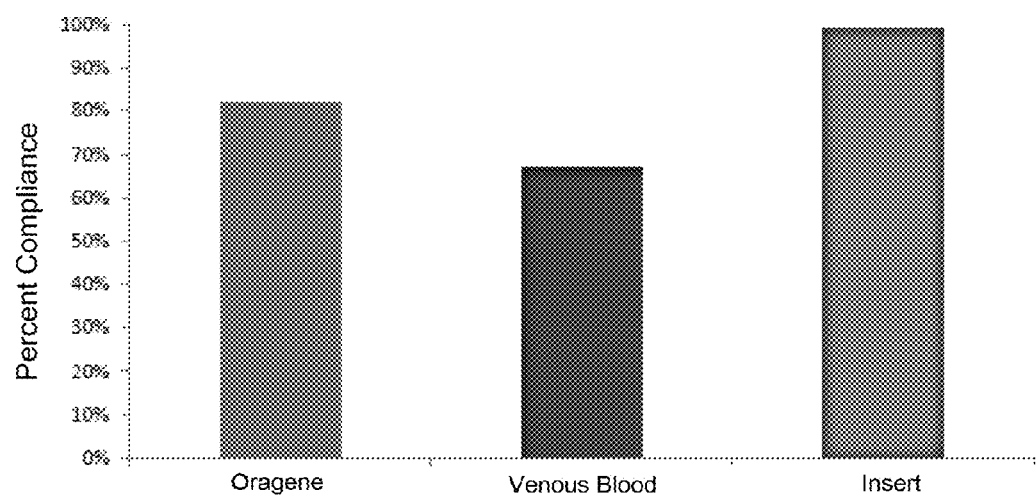
FIG. 20 shows a graph plotting collection method vs. percent compliance.

FIG. 20 shows the compliance of subjects with the collection of saliva samples, venous blood samples, and buccal cell samples. Nearly 100% compliance was observed when subjects submitted buccal cells samples that were collected in combination with the insert. About 80% and about 75% compliance were observed when the subjects submitted saliva and venous blood samples, respectively. Accordingly, these data indicated that higher compliance was achieved with buccal cell collection as compared to saliva and venous blood collection, when the buccal cells were collected with the combination of a swab(s) and the insert.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of collecting a sample from a subject, the method comprising:
   (a) providing a sample recovery and collection device comprising:
      a tube;
      a cap including an O-ring, the cap removably secured to the tube for sealing the tube;
      an insert including a first end having a ring that is adhered to the tube and a second end opposite the first end, the insert including a first leg, a second leg, and a third leg each coupled to and extending from the ring to the second end; and
      an opening extending from the ring to the second end, the insert defining a diameter,
      wherein each of the first, second and third legs includes a plurality of concentric protrusions that project radially from an inside surface of each of the legs;
   (b) contacting a tip of a swab against a body portion of the subject to obtain the sample;
   (c) inserting the swab tip through the opening of the insert; and
   (d) transferring the sample from the swab tip to a solution enclosed within the tube.

2. The method of claim 1, wherein the sample comprises buccal cells.

3. The method of claim 1, wherein inserting further comprises applying pressure to the swab tip to cause the sample to be squeezed from the swab tip into the tube to mix with the solution.

4. The method of claim 1, further comprising:
   (e) contacting a tip of a second swab against the body portion of the subject to obtain a second sample;
   (f) inserting the second swab tip through the opening of the insert; and
   (g) transferring the second sample from the second swab tip to the solution enclosed within the tube.

* * * * *